United States Patent
Viemann et al.

(10) Patent No.: US 11,253,570 B2
(45) Date of Patent: Feb. 22, 2022

(54) S100A8/S100A9-INDUCED IMMUNOTOLERANCE IN NEWBORN SUBJECTS

(71) Applicants: Westfälische Wilhelms-Universität Münster, Münster (DE); Medizinische Hochschule Hannover (MHH), Hannover (DE)

(72) Inventors: Dorothee Viemann, Hannover (DE); Johannes Roth, Münster (DE); Thomas Vogl, Münster (DE)

(73) Assignees: Medizinische Hochschule Hannover (MHH), Hannover (DE); Westfalische Wilhelms-Universität Münster, Münster (DE)

( * ) Notice: Subject to any disclaimer, the term of this patent is extended or adjusted under 35 U.S.C. 154(b) by 43 days.

(21) Appl. No.: 16/347,907

(22) PCT Filed: Nov. 6, 2017

(86) PCT No.: PCT/EP2017/078291
§ 371 (c)(1),
(2) Date: May 7, 2019

(87) PCT Pub. No.: WO2018/083291
PCT Pub. Date: May 11, 2018

(65) Prior Publication Data
US 2019/0374605 A1    Dec. 12, 2019

(30) Foreign Application Priority Data
Nov. 7, 2016 (LU) .......................................... 93291

(51) Int. Cl.
*A61K 38/17* (2006.01)
*A61P 29/00* (2006.01)
*G01N 33/96* (2006.01)
*G01N 33/68* (2006.01)

(52) U.S. Cl.
CPC .......... *A61K 38/1738* (2013.01); *A61P 29/00* (2018.01); *G01N 33/689* (2013.01); *G01N 2333/4727* (2013.01); *G01N 2800/26* (2013.01); *G01N 2800/50* (2013.01)

(58) Field of Classification Search
None
See application file for complete search history.

(56) References Cited

U.S. PATENT DOCUMENTS

2015/0210768 A1 * 7/2015 Roth .................. A61P 3/06
424/139.1

FOREIGN PATENT DOCUMENTS

| WO | 2014037588 A2 | 3/2014 |
| WO | 2015078711 A2 | 6/2015 |
| WO | 2016116881 A1 | 7/2016 |

OTHER PUBLICATIONS

O'Neill, "Targeting signal transduction as a strategy to treat inflammatory diseases," Nature Reviews Drug Discovery 5: 549-563 (2006) (Year: 2006).*
Wang et al., "S100A8/A9 in Inflammation," frontiers in immunology 9:1-14 (2018) (Year: 2018).*
Terrin et al., "S100 A8/A9 protein as a marker for early diagnosis of necrotising enterocolitis in neonates," Arch Dis Child 97:1102 (2012) (Year: 2012).*
Carl et al. (2014) "Sepsis From the Gut: The Enteric Habitat of Bacteria That Cause Late-Onset Neonatal Bloodstream Infections", Clinical Infectious Diseases, 58(9):1211-1218.
Warner et al. (2016) "Gut bacteria dysbiosis and necrotising enterocolitis in very low birthweight infants: a prospective case-control study", The Lancet, 387:1928-1936.
Willers et al. (2020) "S100A8 and S100A9 Are Important for Postnatal Development of Gut Microbiota and Immune System in Mice and Infants", Gastroenterology, 159(6):2130-2145.
Heinemann, et al. (Jun. 2017) "In neonates S100A8/S100A9 alarmins prevent the expansion of a specific inflammatory monocyte population promoting septic shock," The FASEB Journal, 31(3):1153-1164.
Pergialiotis, et al. (2014)"Calprotectin levels in necrotizing enterocolitis: a systematic review of the literature," Inflammation Research, 65:847-852.
Austermann, et al. (2014) "Alarmins MRP8 and MRP14 induce stress tolerance in phagocytes under sterile inflammatory conditions," Cell Reports, 9:2112-2123.
Sağlam, et al. (2015) "Small intestinal lactoferrin and calprotectin levels in different stages of necrotizing enterocolitis in a rat model," Advances in Medical Sciences 60:199-203.
Fassl, et al. (2015) "Transcriptome assessment reveals a dominant role for TLR4 in the activation of human monocytes by the alarmin MRP8," J Immunol, 194:575-583.
Rouǵe, et al. (Jun. 2010) "Fecal calprotectin excertion in peterm infants during the neonatal period," PLoS One, 5(6): 7 pages.
Li, et al. (Mar. 5, 2015) "Fecal calprotectin concentrations in healthy children aged 1-18 months," PLoS One, 10(3) 1371:12 pages.
Ulas, et al. (Jun. 2017) "S100-alarmin-induced innate immune programming protects newborn infants from sepsis," Nature Immunology, 18(6):622-632.
Álvarez-Errico, et al. (Jan. 2015) "Epigenetic control of myeloid cell differentiation, identity and function," Nature Reviews, 15:7-16.

(Continued)

Primary Examiner — Julie Ha
Assistant Examiner — Kristina M Hellman
(74) Attorney, Agent, or Firm — Kagan Binder, PLLC

(57) ABSTRACT

The present application provides for the use of S100A8 or S100A9 homodimer or S100A8/A9 heterodimer in the prevention or treatment of a NF-κB-associated postnatal inflammatory disorder in a newborn subject. Moreover, the present invention relates to a pharmaceutical composition comprising S100A8 or S100A9 homodimer or S100A8/A9 heterodimer and an in vitro method for evaluating the risk of a newborn subject for developing a NF-κB-associated postnatal inflammatory disorder.

17 Claims, 21 Drawing Sheets

Specification includes a Sequence Listing.

(56) References Cited

OTHER PUBLICATIONS

Zhao, et al. (May 27, 2008) "Hyper Innate Responses in Neonates Lead to Increased Morbidity and Mortality After Infection," PNAS, 105(21):7528-7533.
Biswas, et al. (2009) "Endotoxin tolerance: new mechanisms, molecules and clinical significance," Trends in Immunology, 30(10):475-487.
Cuenca, et al. (Jul. 2011) "Critical role for CXC ligand 10/CXC Receptor 3 signaling in the murine neonatal response to sepsis," Infection and Immunity, 79(7):2746-2754.
Cuenca, et al. (2015) "TRIF-dependent innate immune activation is critical for survival to neonatal gram-negative sepsis," J Immunol, 194:1169-1177.
Escoubet-Lozach, et al. (Dec. 2011) "Mechanisms establishing TLR4-responsive activation states of inflammatory response genes," PLoS Genetics, 7(12):14 pages.
Fitzgerald, et al. (Oct. 6, 2003) "LPS-TLR4 signaling to IRF-3/7 and NF-κB involves the toll adapters TRAM and TRIF," Journal of Experimental Medicine,198(7):1043-1055.
Foell, et al. (2004) "Phagocyte-specific calcium-binding S100 proteins as clinical laboratory markers of inflammation," Clinica Chimica Acta, 344:37-51.
Hoebe, et al. (Dec. 2003) "Upregulation of costimulatory molecules induced by lipopolysaccharide and double-stranded RNA occurs by Trif-dependent and Trif-independent pathways," Nature Immunology, 4(12):1223-1229.
Hunter, et al. (1998) "High level expression and dimer characterization of the S100 EF-hand proteins, migration inhibitory factor-related proteins 8 and 14*", Journal of Biological Chemistry, 273(20), Issue of May 15:12427-12435.
Kanagavelu, et al. (Nov. 2015 ) "TIR domain-containing adapter-inducing beta interferon (TRIF) mediates immunological memory against bacterial pathogens," Infection and Immunity 83(11):4404-4415.
Kolb, et al. (2014) "Type I interferon signaling contributes to the bias that toll-like receptor 4 exhibits for signaling mediated by the adaptor protein TRIF," Sci Signal, 7(351):1-30.
Kollmann, et al. (Nov. 16, 2012) "Innate immune function by toll-like receptors: distinct responses in Newborns and the elderly," Immunity, 37:771-783.
Leukert, et al. (May 2005) "Molecular basis of the complex formation between the two calcium-binding proteins S100A8 (MRP8) and S100A9 (MRP14)," Biol. Chem., 386:429-434.
Levy (May 2007) "Innate immunity of the newborn: basic mechanisms and clinical correlates," Nature Reviews, Immunology, 7:379-390.
Lissner, et al. (Jul. 6, 2015) "Age-related gene expression differences in monocytes from human neonates, young adults, and older adults," PLoS One | DOI:10.1371/journal.pone.0132061:18 pages.
Liu, et al. (2015) "Global, regional, and national causes of child mortality in 2000-13, with projections to inform post-2015 priorities: an updated systematic analysis," Lancet, 385:430-440.
Matamoros, et al. (Apr. 2013) "Development of intestinal microbiota in infants and its impact on health," Trends in Microbiology, 21(4):167-173.
Melo et al. (Jan. 2010) "Immune cells and oxidative stress in the endotoxin tolerance mouse model," Braz J Med Biol Res, 43(1):57-67.
Mogensen (Apr. 2009) "Pathogen recognition and inflammatory signaling in innate immune defenses," Clinical Microbiology Reviews, 22(2):240-273.
Roth, et al. (Apr. 2003) "Phagocyte-specific S100 proteins: a novel group of proinflammatory molecules," Trends in Immunology, 24(4):155-158.
Saeed, et al. (Sep. 26, 2014) "Epigenetic programming during monocyte to macrophage differentiation and trained innate immunity," Science, 345(6204):26 pages.
Saliba, et al. (Sep. 11, 2014) "IRF5:RelA interaction targets inflammatory genes in macrophages," Cell Reports 8:1308-1317.
Singh, et al. (Apr. 2013) "Decreased pattern recognition receptor signaling, interferon-signature, and bactericidal/permeability-increasing protein gene expression in cord blood of term low birth weight human newborns," PLoS One, 8(4) | e62845:14 pages.
Takeuchi, et al. (Mar. 19, 2010) "Pattern recognition receptors and inflammation," Cell, 140:805-820.
Viemann, et al. (Jul. 2006) "TNF induces distinct gene expression programs in microvascular and macrovascular human endothelial cell," Journal of Leukocyte Biology, 80:174-185.
Viemann, et al. (2011) "H5N1 virus activates signaling pathways in human endothelial cells resulting in a specific imbalanced inflammatory response," J Immunol, 186:164-173.
Vogl, et al. (1999) "Calcium-induced noncovalently linked tetramers of MRP8 and MRP14 detected by ultraviolet matrix-assisted laser desorption/ionization mass spectrometry," Journal of the American Society for Mass Spectrometry, 10:1124-1130.
Vogl, et al. (2006) "Biophysical characterization of S100A8 and S100A9 in the absence and presence of bivalent cations," Biochimica et Biophysica Acta, 1763:1298-1306.
Vogl, et al. (2007) "Mrp8 and Mrp14 are endogenous activators of toll-like receptor 4, Promoting Lethal, Endotoxin-induced shock," Nature Medicine, 13(9):1042-1049.
Weiss, et al. (2013) "IRF5 is a specific marker of inflammatory macrophages in vivo," Mediators of Inflammation, 2:10 pages.
Yamamoto, et al. (Nov. 2003) "TRAM is specifically involved in the toll-like receptor 4-mediated myD88-independent signaling pathway," Nature Immunology, 4(11):1144-1150.

* cited by examiner

|  | Term | Preterm | Preterm | |
|---|---|---|---|---|
|  |  |  | LONS[2] | w/o LONS |
| Number of infants | 31 | 49 | 13 | 36 |
| Vaginal delivery [%] | 65 | 18 | 23 | 17 |
| Gestational age at birth [weeks][1] | 39.1 (1.0) | 29.7 (4.0) | 28.3 (4.2) | 30.2 (3.9) |
| Birth weight [g][1] | 3607 (469) | 1568 (831) | 1360 (960) | 1650 (776) |
| Gender, female [%] | 40% | 39% | 31% | 42% |
| Apgar index at min 10[1] | 9.9 (0.4) | 8.8 (0.8) | 8.5 (0.7) | 8.9 (0.9) |
| umbilical arterial pH[1] | 7.28 (0.09) | 7.32 (0.07) | 7.33 (0.06) | 7.31 (0.08) |

[1] Mean (± s.d.), [2] day 9 ± 5 of life at diagnosis
LONS: late-onset neonatal sepsis CS = caesarean section
VD = vaginal delivery

S100A8/S100A9-INDUCED IMMUNOTOLERANCE IN NEWBORN SUBJECTS

This application claims priority to International Patent Application No. PCT/EP2017/078921, filed Nov. 6, 2017, and titled "S100A8/S100A9-INDUCED IMMUNOTOLERANCE IN NEWBORN SUBJECTS", which claims the benefit of Luxembourg Patent Application No. 93291, filed Nov. 7, 2016, the disclosures of which are incorporated in their entireties herein by reference. Also, the entire content of the ASCII text file entitled "IPM0094US_Sequence_Listing.txt" created on Aug. 1, 2019, having a size of 9 kilobytes is incorporated herein by reference.

The present invention relates to S100A8 or S100A9 homodimer or S100A8/A9 heterodimer for use in the prevention or treatment of a NF-κB-associated postnatal inflammatory disorder or a postnatal alteration increasing the risk of a NF-κB-associated postnatal inflammatory disorder in a newborn subject. The present invention further relates to a pharmaceutical composition comprising S100A8 or S100A9 homodimer or S100A8/A9 heterodimer for use in the prevention or treatment of a NF-κB-associated postnatal inflammatory disorder or a postnatal alteration increasing the risk of a NF-κB-associated postnatal inflammatory disorder in a newborn subject. Also provided herein is an in vitro method for evaluating the risk of a newborn subject for developing a NF-κB-associated postnatal inflammatory disorder or a postnatal alteration increasing the risk of a NF-κB-associated postnatal inflammatory disorder, the method comprising (a) determining the amount of S100A8/S100A9 heterodimer in a sample from said subject and (b) comparing the result of (a) with a reference value, wherein an increased amount of S100A8/S100A9 heterodimer as compared to a reference value indicates a decreased risk for developing a NF-κB-associated postnatal inflammatory disorder or a postnatal alteration increasing the risk of a NF-κB-associated postnatal inflammatory disorder, and wherein an decreased amount of S100A8/S100A9 heterodimer as compared to a reference value indicates an increased risk for developing a NF-κB-associated postnatal inflammatory disorder or a postnatal alteration increasing the risk of a NF-κB-associated postnatal inflammatory disorder.

Uncontrolled inflammatory processes play an important role in many diseases such as infections, sepsis, septic shock, allergies and autoimmune diseases, as well as chronic diseases such as atherosclerosis. Beside the specific, adaptive immune system unspecific, inflammatory processes of the innate immune system have also been the focus of attention recently. The innate immune system represents the first line of defence against invading pathogens and other external harmful agents. The recognition of conserved structures of various pathogens by specific "Pattern Recognition Receptors" (PRR) is well characterized. PRR include inter alia the family of Toll-like-receptors (TLR), which initiate the activation of the inflammation process against conserved structures of pathogens, also known as "Pathogen Associated Molecular Patterns" (PAMP). Gram-negative bacteria are mainly recognized by TLR4 via the lipid A portion of lipopolysaccharide (LPS), whereas lipoteichoic acid, lipoproteins, and peptidoglycan of gram-positive bacteria are mainly detected by TLR2. However, most gram-positive and gram-negative bacteria can activate additional TLRs via alternative PAMPs present in the cell membrane, cell wall, or intracellularly (Mogensen, Clinical Microbiology Review (2009) 22(2): 240-273).

As an illustrative example, during an infection with gram-negative bacteria, LPS very effectively induces an inflammatory response via the LPS-receptor complex (TLR4/MD2/CD14) in phagocytes, inter alia the induction of pro-inflammatory cytokines such as TNFα and IL-1β (Takeuchi et al., Cell (2010) 140: 805). After ligation, TLR4 binds to the adaptor protein MyD88 and causes activation of NF-κB, inducing a pro-inflammatory cytokine program including TNFα, IL-1β and IL-6 (Takeuchi et al., Cell (2010) 140: 805; Escoubet-Lozach et al., PLoS Genet (2011) 7, e1002401). Interferon regulatory factor 5 (IRF5) consolidates the pro-inflammatory program by cistronic interaction with NF-κB p65 (Weiss et al., Mediators Inflamm (2013) 245804; Saliba et al., Cell Rep (2014) 8: 1308). Via its second adaptor Toll/IL-1R domain-containing adapter inducing IFN-γ (TRIF), TLR4 activates IRF3. IRF3 triggers the secretion of IFN-γ and STAT1 which in turn induces genes like IFNB1, CCLS, CXCL10, and costimulatory molecules such as CD40, CD80, and CD86 by activating the type 1 IFN receptor pathway (Escoubet-Lozach et al., PLoS Genet (2011) 7, e1002401; Fitzgerald et al.; J Exp Med (2003) 198: 1043; Yamamoto et al., Nat Immunol (2003) 4: 1144; Biswas et al., Trends Immunol (2009) 30: 475; Hoebe et al., Nat Immunol (2003) 4: 1223).

Therapeutic approaches of blocking TLR4 are already being examined in clinical studies. Furthermore during the last years so-called "Damage Associated Molecular Pattern molecules" (DAMP) have been identified, which are proteins that are being released by activated or necrotic cells during cell stress. These endogenous ligands or "Alarmins" likewise activate PRR, thereby amplifying the inflammatory immune response and enhancing inflammatory reactions. S100A8 (myeloid related protein 8, MRP8) and S100A9 (myeloid related protein 14, MRP14) are two members of the low-molecular-weight S100 protein family which belong to DAMP proteins and exhibit pro-inflammatory activities in many human diseases, inter alia allergies, autoimmune diseases, rheumatoid arthritis, inflammatory bowel diseases, vasculitis, dermatitis or psoriasis. Both, S100A8 and S100A9 are usually co-expressed in circulating neutrophils and early differentiation stage of monocytes, as well as in keratinocytes and epithelial cells under inflammatory conditions. During activation of phagocytes, S100A8 and S100A9 are released suggesting intra—as well as extracellular functions during inflammation.

S100A8 and S100A9 can form non-covalently associated oligomers, such as monovalent S100A8 or S100A9 homodimers and S100A8/A9 heterodimers (MRP8/14, calprotectin), as well as even higher oligomeric forms (Hunter and Chazin, J Biol Chem 11998) 273(20): 12427-35, Vogl et al., J Am Soc Mass Spectrom (1999) 10:1124-1130). In this context, distinct hydrophobic amino acids have been identified as directly involved in S100A8/S100A9 dimer formation (Leukert et al., Biol Chem (2005), 386: 429-434). However, simple mixing of both S100A8 and S100A9 subunits is not sufficient for proper heterodimer complex formation, but steps of denaturation/renaturation are necessary for the recombinant complex to show identical properties as S100A8/S100A9 as obtained from granulocytes (Vogl et al., BBA (2006) 1763: 1298-1306, Leukert et al., Biol Chem (2005), 386: 429-434, Foell et al., Clin Chim Acta (2004), 344(1-2): 37-51, Roth et al., Trends Immunol (2003), 24: 383-397. S100A8 and S100A9 have also been found to oligomerize to (S100A8/S100A9)$_2$ heterotetramers. Tetramer formation is strictly dependent on the presence of calcium, and in the absence of calcium, heterodimers are the preferred forms of S100A8 and S100A9. The dimer form is known to bind four $Ca^{2+}$-ions, while the $(S100A8/S100A9)_2$ heterotetramer binds eight $Ca^{2+}$-ions. S100A8 and S100A9 represent the major calcium-binding proteins in phagocytes, and both proteins regulate migration of these cells via modulation of tubulin polymerization. In biological sample, S100A8 and S100A9 generally exist as heterodimers and tetramers. S100A8/S100A9 function as endogenous TLR4 ligand and due to their specific and high expression at sites of inflammation, one can refer them as a prime candidate for the TLR4/MD2/CD14-driven inflammatory processes. Accordingly, S100A8/S100A9 heterodimers may be considered as early amplifier of inflammation, inducing pro-inflammatory response in endothelial cells and phagocytes. However, $(S100A8/S100A9)_2$ tetramerization seems to lead to formation of inactive $(S100A8/S100A9)_2$ tetramer complexes, which are not able to interact with the TLR4 receptor and thus block the S100A8/S100A9 activity and thus the pro-inflammatory TNFα-releasing pathway (WO2014/037588).

In adults, the S100A8/S100A9 serum level is increased in many inflammatory disorders and the acute effect of accumulation of S100A8/S100A9 is according to the definition as "Alarmins" the amplification of inflammatory processes up to septic shock (Vogl et al., Nat. Med. (2007) 13: 1042-1049). In this regard several diagnostic and therapeutic strategies for detecting and inhibiting said protein complex have been described (WO2014/037588, WO2015/078711, WO2004/110366, U.S. Pat. Nos. 8,916,163, 9,226,947). Further, the use of S100A8/S100A9 mRNA in suppressing cell proliferation and inhibiting infection of epithelial cells has been reported (WO2014/110366) as well as the use of S100A8/S100A9 heterodimers or S100A8/S100A9 polypeptides for treating and/or preventing skin diseases or degenerative, neurological or autoimmune diseases (WO2002/088181, WO2001/05422).

Lately, it has been reported that under in vitro conditions the endogenous S100A8/S100A9 derivatives induce stress tolerance in phagocytes of sterile inflammation, polytrauma and burn trauma patients. In this regard it has been shown in vitro that pre-treatment of human and murine monocytes with S100A8 or S100A9 homodimer or S100A8/S100A9 heterodimer for at least 24 hours and subsequent stimulation of said monocytes with LPS leads to an attenuated release of several cytokines release. In this respect S100A8/S100A9 derivatives showed a tolerizing effect. Further, in an endotoxin mouse model, the pre-treatment with S100A8/A9 heterodimer significantly protects mice against LPS-induced shock similar to classically induced LPS tolerance and this effect results in enhanced survival to septic shock (Melo et al., Braz. J. Med. Biol. Res. (2010) 43: 57-67). Accordingly, the long-term effect of S100A8/S100A9 derivatives on the TLR4 receptor complex seem to lead to microbial hyporesponsivity of phagocytes called "stress tolerance" (Austermann et al., Cell Reports (2014) 9: 1-12; Biswas et al., Trends Immunol (2009) 30: 475). Further, it has been shown that healthy term neonates massively release S100A8/S100A9 at birth and increased concentrations of S100A8/S100A9 could be detected in the serum and in the stool of term newborn (Austermann et al., Cell Reports (2014) 9: 1-12).

In adults, the endotoxin-tolerance (ET) seems to be particularly linked to the pro-inflammatory MyD88-dependent transcriptional program, whereas TRIF-dependent genes were shown to be involved in the induction of ET. For the neonatal situation, the roles of MyD88- and TRIF-dependent pathways with respect to the LPS response and postnatal maturation processes are however not yet defined. Further, although previous studies indicate that endogenous S100A8/S100A9 derivatives may induce a state of hypoinflammation in neonatal phagocytes in vitro, it remains still completely unclear whether the hypoinflammatory state of neonatal phagocytes is disadvantageous, promoting the susceptibility of neonates to infections, or whether it is beneficial in preventing systemic hyperinflammatory response syndromes in the course of developing sepsis (Austermann et al., Cell Reports (2014) 9: 1-12).

Accordingly, the role of S100A8/S100A9 derivatives in the neonatal immune system in vivo, in particular the postnatal role of S100A8/S100A9 in newborn subjects such as premature subject still remains unclear. However, premature also called preterm birth (defined as birth before 37 weeks gestation) is the most important risk factor for perinatal mortality and morbidity (Deutsche Gesellschaft für Gynäkologie und Geburtshilfe: Leitlinie 015/025, Medikamentöse Wehenhemmung bei drohender Frühgeburt). In 2011 in Germany 9% of all children were born before consummated 37th week of pregnancy (AQUA—Institut für angewandte Qualitätsförderung und Forschung im Gesundheitswesen GmbH. Bundesauswertung zum Verfahrensjahr 2010 16/1—Geburtshilfe). The rate of premature births has remained stable over the past decade. However, the number of extreme premature births, i.e. before 28 weeks of gestation, has increased by 65%. The reasons thereof have not yet been analyzed, but seem to derive from known demographic risk factors, such as the increase in maternal age in pregnancy.

Especially premature births and children with a very low birth weight are at high risk of developing sepsis, i.e. a bacterial infection of the blood. According to estimations of the WHO, in 2011 about 5% of all deaths under the age of five are consequence of a neonatal septic disease (WHO-UNICEF Child Heath Epidemiology Reference Group (CHERG) estimates). Thus neonatal sepsis is a major risk factor for childhood mortality in this age group (Liu et al., Lancet (2015) 385: 430). One hallmark of neonatal sepsis is an extremely rapid course with a hyperinflammatory response (Zhao et al., Proc Natl Acad Sci USA (2008) 105: 7528). Newborns with sepsis are usually listless, do not feed well, and often have a low body temperature. Other symptoms may include pauses in breathing (apnea), fever, pale color, and poor skin circulation, with cool extremities, abdominal swelling, vomiting, diarrhea, seizures, jitteriness, and jaundice. A definite diagnosis is made only if bacteria are identified in a culture of the newborn's blood. While awaiting blood culture results, doctors give intravenous antibiotics to newborns with suspected sepsis. Once the specific organism has been identified, the type of antibiotic can be adjusted. In addition to antibiotic therapy, other treatments may be needed, such as use of a ventilator, intravenous fluids, and support of blood pressure and circulation. However, antibiotic therapy results in changes in the normal development of the intestinal microbiota, generally coinciding with a decrease in phylogenetic diversity (Matamoros et al., Trends Microbiol. (2013) 21(4):167-73). Further, also therapeutic use of immunoglobulin preparations containing antibodies that may help the body during sepsis to neutralize bacterial toxins are controversially discussed in the art.

Premature infants and newborn subjects delivered by Caesarean section are at much higher risk of both early-onset (developed in the first 3 days of life) and late-onset (developed after 3 days of life) sepsis than are infants born at full term and by vaginal birth. Currently, the high susceptibility of human neonates is assigned to an immaturity of the neonatal immune system because responses towards PAMPs, particularly LPS, were found to be impaired in innate immune cells derived from newborn subjects. In fact, the impaired innate immune response found experimentally e.g. in response to lipopolysaccharide (LPS) derived from gram-negative bacteria via TLR4 promoted the concept of immaturity (Kollmann et al., Immunity (2012) 37: 771; Levy, Nat Rev Immunol (2007) 7: 379). However, this line of argumentation is not consistent with the clinical hallmark of neonatal sepsis, which is a hyperdynamic course with hyperinflammatory immune responses. The unexplained clinical observation in this context is the rapid course of neonatal sepsis characterized by a hyperdynamic immune response with elevated levels of IL-6, IL-1β and TNF-α. Such overt inflammatory responses contradict a concept of immaturity but suggest the existence of alternative immune-regulation at birth. Further, since this inconsistency of experimental and clinical findings is currently unsolved, the development of better therapeutic strategies is prevented.

Thus, there is a need in the art to better understand the current discrepancy between clinical and experimental observations and to comprehensively compare the TLR-dependent signaling of human adult and neonatal monocytes induced by gram-negative and gram-positive bacteria. Further, there is still a need in the art for new means and methods which allow for the prevention and treatment of postnatal inflammatory disorders such as newborn sepsis, necrotizing enterocolitis, and bronchopulmonary dysplasia in newborn subjects. Equally, there is a demand for the prevention and treatment of postnatal alterations such as disturbed microbiome development which might increase the risk of postnatal inflammatory disorders. Thus, there is a demand for therapeutic compositions and methods for the prevention and treatment of postnatal inflammatory disorders or postnatal alterations which may directly cause postnatal inflammatory disorders in a newborn subject. Such therapeutic approaches should allow for a significant reduction of the risk of newborn subjects, in particular premature subjects and newborn subjects delivered by Caesarean section to develop said postnatal inflammatory disorders. Thus, said means and methods should also provide a precise therapeutic tool for the prevention and treatment of said postnatal inflammatory disorders associated with a hyperdynamic immune response. Moreover, there is a need in the art for a method which would allow for the evaluation of the risk of a newborn subject for developing a postnatal inflammatory disorder or a postnatal alteration which can cause said postnatal inflammatory disorder. Such a method would allow to recognize and reflect the status and/or the progression of a postnatal inflammatory disorder or a postnatal alteration which can cause said postnatal inflammatory disorder in a newborn subject, in particular a premature newborn subject or a newborn subjects delivered by Caesarean section. The technical problem underlying the present application is thus to comply with this need. The technical problem is solved by providing the embodiments reflected in the claims, described in the description and illustrated in the examples and figures that follow.

Provided herein are methods and compounds that are suitable for use in the prevention or treatment of postnatal inflammatory disorders or postnatal alteration increasing the risk of a postnatal inflammatory disorder in a newborn subject. Particularly provided are methods and compounds suitable for use in the prevention or treatment of NF-κB-associated postnatal inflammatory disorders, such as TLR4- and/or TLR2-mediated postnatal inflammatory disorders in newborn subjects that are prone to hyperinflammatory immune responses. Equally provided are methods and compounds suitable for use in the prevention or treatment of postnatal alteration increasing the risk of a NF-κB-associated postnatal inflammatory disorder in a newborn subject. In contrast to conventional therapeutic approaches, the methods or uses as described herein involves administering endogenous TLR4-ligands of the low-molecular-weight S100 protein family, namely S100A8 or S100A9 homodimers or S100A8/S100A9 heterodimers, to said newborn subject. Thus, while conventional therapeutic approaches aim at eliminating the bacterial infection as cause of the postnatal inflammatory disorder by antibiotic treatment of the newborn subject suffering from a postnatal inflammatory disorder, the methods and uses provided herein aim at immunotolerance which does not lead to an amplification of immune responses and subsequent inflammatory disorders during postnatal bacterial colonization.

Thus, the present invention describes in this connection the possibility of the prevention or treatment of NF-κB-associated postnatal inflammatory disorders or a postnatal alteration which increase the risk of a NF-κB-associated postnatal inflammatory disorder in a newborn subject by the use of S100A8/S100A9 derivatives leading to an improved long-term survival rate of newborn subjects. The provided methods and uses are in this regard particularly suitable for premature newborn subjects and newborn subjects delivered by Caesarean section. Thereby the provided uses and methods are substantially more specific than conventional approaches.

Using transcriptomic, epigenetic, bioinformatic and immunological approaches, the present inventors demonstrated that high levels of alarmins (endogenous TLR4-ligands) at birth transiently elevate the baseline expression of MyD88-dependent genes, thereby decreasing the capacity to up-regulate this gene program after stimulation by LPS. Conversely, neonatal monocytes strongly activate TRIF-dependent regulatory genes that are not yet expressed at baseline. This process is epigenetically regulated, as basal acetylation marks at MyD88-dependent gene loci could be observed in neonatal monocytes but not at TRIF-dependent loci (FIG. 1-4). The latter acquire epigenetic transcription marks but not before challenges with LPS. During the first year of life, the expression tonus of TRIF-dependent genes gradually increases, shifting the balance between TRIF- and MyD88-dependent gene regulation toward the adult phenotype. Thus, the presented data provide evidence that alarmin-mediated tolerization of MyD88-dependent genes at birth is essential to prevent hyperinflammatory responses because regulatory TRIF-dependent genes require initiation. These findings are consistent with a differentially regulated but not impaired immune response at birth. Thus, the present inventors predict that diminished alarmin-mediated tolerization of MyD88-dependent genes with simultaneous deficits or delays in TRIF-dependent gene expression paves the way for hyperinflammatory immune responses, putting newborns at increased risk for fatal sepsis.

Further, the presented data provide evidence that the vulnerability of neonates is not a matter of immaturity but rather linked to the balancing act of alternative regulation during adaptation of the neonatal innate immune system. In detail, the novel findings are that in strong contrast to adult monocytes, monocytes from human newborns react to LPS stimulation with a very strong induction of TRIF-dependent and mostly regulatory genes, while the expression of MyD88-dependent, mostly pro-inflammatory genes are not strongly elevated. Also, the differential induction of gene expression towards LPS is at least in part explained by a completely different basal expression state of MyD88-dependent inflammatory and TRIF-dependent regulatory genes in human adult as compared to neonatal monocytes. For the first time, the differential regulation of TRIF- and MyD88 genes at birth could be linked to elevated levels of the endogenous alarmins S100A8 and S100A9 known to be massively elevated at birth in healthy newborns (Austermann et al., Cell Rep (2014) 9(6):2112-23). However, as shown by the present inventor, said alarmins are much less elevated in premature subjects (FIG. 8) and newborn subjects delivered by Caesarean section (FIG. 9). Thus, pre-activation of MyD88—but not TRIF-dependent genes by the endogenous alarmins S100A8 and S100A9 at term and vaginal birth induces a tolerant state of hyporesponsiveness, preventing NF-θB-associated hyperinflammatory responses. Further, molecularly, this specific transcriptional and functional state of neonatal monocytes is due to the altered activation of NF-κB and high basal IRF5 activity and differences in epigenetic regulation at MyD88- and TRIF-dependent target genes, as assessed by histone modifications at the respective gene loci, which ultimately results in global differences in gene transcription and function. While the regulation of MyD88-dependent genes can be altered by the in vitro culture of neonatal monocytes, the gene regulation of TRIF-dependent genes as observed in adult monocytes could not be acquired in vitro. More importantly, when analyzing changes in gene regulation in vivo in 127 healthy infants during their first year of life, it could be clearly demonstrated that the basal gene expression program of TRIF-dependent genes was steadily established during this prolonged period of time (FIG. 1-4).

These findings strongly support the hypothesis that the previously suggested impaired LPS response of the newborn immune system is explained by a transient birth-related alarmin-induced state of unresponsiveness, particularly for MyD88-dependent genes. It can be suggested that this is an essential mechanism in neonates to prevent NF-κB-associated hyperinflammatory responses to gram-positive and gram-negative bacteria as long as the expression tonus of regulatory TRIF-dependent genes is still low after birth. However, insufficient alarmin-induced pre-activation of MyD88-dependent pro-inflammatory genes and impaired or delayed reprogramming of TRIF-dependent regulatory genes renders neonates, in particular premature neonates and newborn subjects delivered by Caesarean section, susceptible to hyperinflammatory immune responses, thereby increasing the sepsis risk in this newborn subjects. Thus, alarmin-induced pre-activation of MyD88-dependent but not TRIF-dependent genes by the administration of alarmins such as S100A8/S100A9 derivatives to a newborn subject at birth seems to induce a tolerant state of hyporesponsiveness to gram-positive and gram-negative bacteria, thereby preventing NF-κB-associated hyperinflammatory responses and postnatal inflammatory disorders. Accordingly, as shown by the inventors of the present invention, a strong release of S100A8 and S100A9 in newborns does not induce an amplification of inflammatory disorders, but induces a stress tolerance leading to an improved long-term survival rate, confirming that S100A8 and S100A9 belong to the tolerance-inducing factors in the neonatal immune system.

In this regard it could be shown that in premature newborn subjects the level of S100A8/S100A9 in the blood cord of newborns is significantly lower than the S100A8/S100A9 level in the blood cord of newborn subjects with a normal gestational age (FIG. 8). Further, it was found that the S100A8/S100A9 serum level in newborn subjects delivered by Caesarean section is significantly lower than in subjects born via vaginal delivery (FIG. 9). Instead, a massively high concentration of S100A8/S100A9 derivatives could be detected in breast milk (FIG. 10). Thus, these observations possibly describe an overriding principle to prevent extreme inflammatory reactions on postnatal bacterial settlements of newborn subjects, in particular premature subjects and Caesarean newborn subjects delivered by Caesarean section. Accordingly, the present invention describes in this connection the possibility of a preventive use of endogenous alarmins such as S100A8/S100A9 derivatives against the formation of NF-κB-associated postnatal inflammatory disorders in consequence of the newborn response towards Pathogen Associated Molecular Patterns (PAMPs), particularly LPS, such as sepsis, necrotizing enterocolitis, and bronchopulmonary dysplasia, or postnatal alterations which in consequence of the newborn response towards PAMPs directly increase the risk of the formation of a NF-κB-associated postnatal inflammatory disorder, such as disturbed microbiome development.

Additionally, it was found out by the present inventors in in vivo experiments with S100-knock-out mice that substitution with S100A8/S100A9 heterodimer or S100A8 homodimer leads in both an endotoxin (LPS administration) model (FIG. 5) as well as a staphylococcus/sepsis model (FIG. 6) to a significantly elevated survival rate of said animals, which further supports the hypothesis of an alarmin-induced state of hyporesponsiveness to gram-positive and gram-negative bacteria in newborn subjects at birth. In this respect also the bacterial load of liver, lung and kidney was significantly reduced in said animals when pre-treated with S100A8/S100A9 derivatives prior to the test series (FIG. 7). Surprisingly, the highest efficacy could be observed for the S100A8 monomer, which seems to be even more efficient than the S100A8/S100A9 heterodimer (FIG. 5 and FIG. 6). Accordingly, the preventive and therapeutic use of S100A8 homodimer seems to be highly recommendable for achieving the desired effect of stress toleration in newborn subjects.

It had been reported before that human cord blood monocytes exhibit a significantly increased secretion of S100A8/S100A9 heterodimers (calprotectin) at birth and increased concentrations of S100A8/S100A9 complex could be detected in the serum and the stool of newborn. However the exact mechanism and the explanation of the suggested impaired LPS response of the newborn immune system by a transient birth-related alarmin-induced state of unresponsiveness, particularly for MyD88-dependent genes was still missing up to now. Moreover, the preventive or therapeutic use of S100A8/S100A9 derivatives in newborn subjects, in particular premature newborn subjects or newborn subjects delivered by Caesarean section had not been described or suggested before. Rather the data presented by the present inventors indicate that the release of the endogenous TLR4 ligands S100A8 and S100A9 seem to represent an overriding, essential principle at birth to induce tolerance and resistance to pro-inflammatory mediators, which enables a postnatal bacterial colonization without inflammatory response. Interestingly it was found that S100A8/S100A9 derivatives in premature born human subjects and neonates after Cesarean section are significantly less released than in timely and vaginally delivered neonate, which correlates with the known disturbed microbiome development in both groups.

Based on the above described findings, the present invention aims at the use of S100A8/S100A9 derivatives in the prevention or treatment of a NF-κB-associated postnatal inflammatory disorders or a postnatal alteration which leads to an increased risk of a NF-κB-associated postnatal inflammatory disorder in a newborn subject. In particular, the above data prompt to the preventive and therapeutic use of the S100A8/S100A9 heterodimer complex and S100A8 or S100A9 homodimers in newborn subjects for the prevention, amelioration or treatment of sepsis, necrotizing enterocolitis, bronchopulmonary dysplasia, and disturbed microbiome development, thereby suggesting a systemic and oral administration. Although it had been reported before that human cord blood monocytes exhibit in vitro a significantly increased secretion of S100A8/S100A9 heterodimers (calprotectin), the therapeutic or preventive use of the TLR4 ligands S100A8 and S100A9 for tolerance induction of the neonatal immune system in the context of environmental adaptation had not been described or suggested so far.

Accordingly, in a first aspect, the present invention relates to S100A8 or S100A9 homodimer or S100A8/A9 heterodimer for use in the prevention or treatment of a NF-κB-associated postnatal inflammatory disorder or a postnatal alteration increasing the risk of a NF-κB-associated postnatal inflammatory disorder in a newborn subject. The term "S100A8 or S100A9 homodimer" as used herein refers to the dimer complex consisting of either two S100A8 or two S100A9 monomers. The term "S100A8/S100A9 heterodimer" refers to the dimer complex consisting of one S100A8 monomer and one S100A9 monomer. As outlined before, S100A8 and S100A9 belong to the calcium-binding cytosolic S100 proteins characterized by two calcium-binding EF hands with different affinities for calcium connected by a central hinge region: a high affinity site at the C terminus (EF-hand II) and a low affinity site at the N terminus (EF-hand I). The EF-hand motifs have two a-helices flanking a central calcium-binding loop, thus resulting in a classical helix-loop-helix motif. S100A8 and S100A9 can form monovalent homodimers and a heterodimer known as S100A8/A9 (MRP8/14, calprotectin), as well as even higher oligomeric forms (Hunter and Chazin, J Biol Chem (1998) 273(20): 12427-35, Vogl et al., J Am Soc Mass Spectrom (1999) 10:1124-1130). In this context, distinct hydrophobic amino acids have been identified as directly involved in S100A8/S100A9 dimer formation (Leukert et al., Biol Chem (2005), 386: 429-434). However, simple mixing of both S100A8 and S100A9 subunits is not sufficient for proper heterodimer complex formation, but steps of denaturation/renaturation are necessary for the recombinant complex to show identical properties as S100A8/S100A9 as obtained from granulocytes (Vogl et al., BBA (2006) 1763: 1298-1306, Leukert et al., Biol Chem (2005), 386: 429-434, Foell et al., Clin Chim Acta (2004), 344(1-2): 37-51, Roth et al., Trends Immunol (2003), 24: 383-397. However, under inflammatory conditions the S100A8 or S100A9 homodimers and S100A8/S100A9 heterodimers seem to be the more relevant forms of S100A8/S100A9 complexes, having pro-inflammatory effects by interacting with the TLR4 receptor as described in detail in WO2014037588, while $(S100A8/S100A9)_2$ tetramerization seems to lead to formation of inactive $(S100A8/S100A9)_2$ tetramer complexes, which are not able to interact with the TLR4 receptor.

According to the present invention, S100A8 homodimers, S100A9 homodimers and S100A8/S100A9 heterodimers are equally applicable for the methods and uses described herein. However, as shown in in vivo experiments with S100-knock-out mice, substitution and pre-treatment with S100A8 homodimer had surprisingly the highest efficacy and lead in both the endotoxin (LPS administration) model and the Staphylococcus aureus sepsis model to the best survival rate of said animals and a significantly reduced bacterial load of different tissues (FIG. 5-7). Thus, it is particularly preferred to apply highly effective S100A8 homodimers when used in the prevention or treatment of a NF-κB-associated postnatal inflammatory disorder or a postnatal alteration increasing the risk of a NF-κB-associated postnatal inflammatory disorder in a newborn subject according to the present invention.

The term "prevention" or "preventing a disorder" as used herein is not intended as an absolute term. Instead, prevention of a NF-κB-associated postnatal inflammatory disorder or a postnatal alteration increasing the risk of a NF-κB-associated postnatal inflammatory disorder may also refer to delay of onset, reduced frequency of symptoms, decreased probability or reduced severity of symptoms associated with said disorder in a newborn subject. In a preferred embodiment, prevention of a NF-κB-associated postnatal inflammatory disorder or a postnatal alteration increasing the risk of a NF-κB-associated postnatal inflammatory disorder may refer to a complete suppression of onset of said disorder in a newborn subject, i.e. said newborn subject will not develop a NF-κB-associated postnatal inflammatory disorder or a postnatal alteration increasing the risk of a NF-κB-associated postnatal inflammatory disorder. Prevention therefore refers to a broad range of prophylactic measures for preventing any of the NF-κB-associated postnatal inflammatory disorders or postnatal alterations increasing the risk of a NF-κB-associated postnatal inflammatory disorder in a newborn subject as described elsewhere herein that will be understood by those in the art. In some circumstances, the severity of symptoms is reduced to non-pathological levels, e.g. so that the newborn subject does not need an antibiotic therapy or a therapy with immune preparations.

Similarly, the term "treating" or "treating a disorder" is not intended to be an absolute term. In some circumstances, the S100A8 or S100A9 homodimer or S100A8/S100A9 heterodimer according to the invention seek to reduce in a newborn subject symptoms associated with a NF-κB-associated postnatal inflammatory disorder, in particular hallmarks of neonatal sepsis, necrotizing enterocolitis, and bronchopulmonary dysplasia as described elsewhere herein. Equally, the S100A8 or S100A9 homodimer or S100A8/S100A9 heterodimer according to the invention seek to reduce in a newborn subject symptoms associated with a postnatal alteration increasing the risk of a NF-κB-associated postnatal inflammatory disorder, in particular hallmarks of a disturbed microbiome development in a newborn subject as described elsewhere herein. In some circumstances, treatment with S100A8 or S100A9 homodimer or S100A8/S100A9 heterodimer according to the present invention leads to an improved prognosis or a reduction in the frequency or severity of symptoms. Thus, the terms "treat", "treatment" or "treating" as used herein generally refer to the medical therapy of any newborn human or other newborn animal subject in need thereof. The terms "treat", "treatment" "treating" further means to reduce, ameliorate, stabilize, or inhibit the progression of a disease and/or symptoms associated therewith in a subject. Said subject is expected to have undergone physical examination by a medical or veterinary medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be palliative, symptomatic and/or curative. In terms of the present invention, palliative, symptomatic and/or curative treatments may represent separate aspects of the present invention.

In the context of the present invention, the postnatal inflammatory disorder is characterized by an increased activation of NF-κB, inducing the release or accumulation of pro-inflammatory cytokines such as TNFα, IL-1β, IL-8 and IL-6 in said newborn subject (Takeuchi et al., Cell (2010) 140: 805, Escoubet-Lozach et al., PLoS Genet (2011) 7, e1002401). Further, the postnatal inflammatory disorder is characterized by increased concentrations of extracellular S100A8/S100A9 heterodimer complexes which can be detected in a sample from said newborn subject. Accordingly, in another aspect, the present invention also relates to an in vitro method for evaluating the risk of a newborn subject for developing a NF-κB-associated postnatal inflammatory disorder or a postnatal alteration increasing the risk of a NF-κB-associated postnatal inflammatory disorder in a newborn subject, the method comprising (a) determining the amount of S100A8/S100A9 heterodimer in a sample from said subject and (b) comparing the result of (a) with a reference value, wherein an increased amount of S100A8/S100A9 heterodimer as compared to a reference value indicates a decreased risk for developing a NF-κB-associated postnatal inflammatory disorder or a postnatal alteration increasing the risk of a NF-κB-associated postnatal inflammatory disorder, and wherein an decreased amount of S100A8/S100A9 heterodimer as compared to a reference value indicates an increased risk for developing a NF-κB-associated postnatal inflammatory disorder or a postnatal alteration increasing the risk of a NF-κB-associated postnatal inflammatory disorder. Preferably, the described method is applied for a premature newborn subject or a newborn subject delivered by Caesarean section.

The term "comparing the results with a reference value" as used herein means that said sample can be compared to a single reference sample or a plurality of reference samples, such as a sample from a reference subject, in any suitable manner. The term "reference" as use herein can be equally substituted by the term "control". Accordingly, the method described herein comprises comparing the amount of S100A8/S100A9 heterodimer in a sample from said newborn subject to the amount of S100A8/S100A9 heterodimer in a reference sample. Said reference or control sample is preferably a sample of a newborn subject suspected to or known to not suffer from a NF-κB-associated postnatal inflammatory disorder or a postnatal disorder increasing the risk of a NF-κB-associated postnatal inflammatory disorder. Thus, the control measurement in this document also referred to as a reference measurement, may be a measurement that is carried out on a sample from a subject known not to suffer from a NF-κB-associated postnatal inflammatory disorder or a postnatal alteration increasing the risk of a NF-κB-associated postnatal inflammatory disorder. In some embodiments a respective reference measurement is carried out on a (control) sample from a subject that is age-matched. In some embodiments such a reference measurement is carried out on a sample from the same subject, taken at a previous point of time. In a method as disclosed herein the amount of S100A8/S100A9 heterodimer complex formed, for instance determined in a sample, may be compared to such a reference measurement. A respective method according to the present invention may also include the measurement of a corresponding S100A8/S100A9 heterodimer complex and comparing the obtained result to a threshold value. A threshold value may for example be a value set to decide whether a S100A8/S100A9 heterodimer complex is formed or not. A threshold value may also be a value set to decide whether a newborn subject suffers from a NF-κB-associated postnatal inflammatory disorder or a postnatal alteration increasing the risk of a NF-κB-associated postnatal inflammatory disorder or not.

As an illustrative example, the level of S100A8/S100A9 heterodimer in a control or reference sample can be characterized by an average (mean) value coupled with a standard deviation value, for example at a given time point. In some embodiments the level of S100A8/S100A9 heterodimer in a subject may be considered increased or decreased when it is one standard deviation or more higher or lower than the average value of the corresponding heterodimer/tetramer determined in one or more control samples. In some embodiments the determined level of S100A8/S100A9 heterodimer is regarded as increased or decreased where the obtained value is about 1.5 standard deviations higher or lower, including about two, about three, about four or more standard deviations higher or lower than the average value determined in a control sample. In some embodiments the determined amount of S100A8/S100A9 heterodimer is regarded as different where the obtained value is about 1.2 times or more higher or lower, including about 1.5 times, about two fold, about 2.5-fold, about three fold, about 3.5 fold, about 4-fold, about 5-fold or more higher or lower than the protein level determined in a control sample.

The term "determining" when used herein includes variations like detecting, qualifying, semi-qualifying or, as the case may be, diagnosing etc. The term "detect" or "detecting", as well as the term "determine" or "determining" when used in the context of a S100A8/S100A9 heterodimer complex refers to any method that can be used to identify the presence of a protein complex released or expressed by a cell. When used herein in combination with the words "level", "amount" or "value", the words "determine" or "determining" or "detect" or "detecting" are understood to refer to a quantitative as well as a qualitative level. In some embodiments the determination of a S100A8/S100A9 heterodimer in a sample may be a method of determining the level (quantitative or semi-quantitative) of S100A8/S100A9 heterodimer by comparing the level of S100A8/S100A9 heterodimer in the sample with the level of S100A8/S100A9 heterodimer standard.

"Determining" or "quantifying" the amount of S100A8/S100A9 heterodimer complex or any other form of S100A8/S100A9 derivatives in a biological sample can be carried out by way of any suitable technique available and known to those skilled in the art. In some embodiments determining the amount of S100A8/S100A9 heterodimer in a biological sample comprises the use of mass spectrometry. When applying mass spectrometry, the S100A8/S100A9 heterodimer is chemically identified and analyzed in a sample by measuring the mass-to-charge-ratio and abundance of gas-phase. Mass spectrometry works by ionizing chemical compounds to generate charged molecules or molecule fragments and measuring their mass-to-charge ratios. In this regard, spectra are used to determine the elemental or isotopic signature of a sample, the masses of particles and of molecules, and to elucidate the chemical structures of molecules. In some embodiments determining the amount of S100A8/S100A9 heterodimer complex in a biological sample comprises the use of aptamer-target-binding technology. When applying aptamer-target-binding technology, S100A8/S100A9 heterodimers are identified by a class of small nucleic acid ligands (aptamers). In some embodiments the aptamers are composed of RNA having high specificity and affinity for their targets. In some embodiments the aptamers are composed of single-stranded DNA oligonucleotides having high specificity and affinity for their targets. Similar to antibodies, aptamers interact with their targets by recognizing a specific three-dimensional structure and are thus termed "chemical antibodies." In contrast to protein antibodies, aptamers offer unique chemical and biological characteristics based on their oligonucleotide properties. In other embodiments "determining" or "quantifying" the amount of S100A8/S100A9 heterodimer complex in a sample comprises the use of an immunoglobulin having binding specificity to S100A8/S100A9 heterodimer. Examples of suitable immunoassay techniques in this regard are radiolabel assays such as a Radioimmunoassay (RIA) or enzyme-immunoassay such as an Enzyme Linked Immunosorbent Assay (ELISA), Luminex®-assays, precipitation (particularly immunoprecipitation), a sandwich enzyme immune test, an electro-chemiluminescence sandwich immunoassay (ECLIA), a dissociation-enhanced lanthanide fluoro immuno assay (DELFIA), a scintillation proximity assay (SPA), turbidimetry, nephelometry, latex-enhanced turbidimetry or nephelometry, or a solid phase immune test. Further methods known in the art (such as gel electrophoresis, 2D gel electrophoresis, SDS polyacrylamide gel electrophoresis (SDS-PAGE), and Western Blotting, can be used alone or in combination with labelling or other detection methods as described herein.

The term "sample" when used as regards the methods of the present invention relates to a material or mixture of materials, typically but not necessarily in liquid form, containing one or more analytes of interest. Preferably, the sample of the present invention is a biological sample. The term "biological sample", as used herein, refers to a sample obtained from an organism or from components (e.g., cells) of an organism, preferably a newborn subject. The sample may be of any biological tissue or fluid. Frequently the sample will be a "clinical sample" which is a sample derived from a patient. The sample as used according to said method include but are not limited to a serum sample, a plasma sample, an urine sample, a fecal sample, a saliva sample, a tracheal secretion sample, a bronchoalveolar fluid sample, a tear fluid sample, or a tissue extract sample. Biological samples from a newborn subject may be obtained by an individual undergoing a self-diagnostic test (e.g., blood glucose monitoring) or by a trained medical professional through a variety of techniques including, for example, aspirating blood using a needle or scraping or swabbing a particular area. Methods for collecting various biological samples are well known in the art.

In the context of the present invention, the term "evaluating the risk" refers to any procedure or method used in vitro to assess whether or not a newborn subject has an increased probability to suffer from a NF-κB-associated postnatal inflammatory disorder or a postnatal alteration increasing the risk of a NF-κB-associated postnatal inflammatory disorder after birth. In this context, "evaluating the risk" particularly refers to any procedure or method used in vitro to assess whether or not a newborn subject has an increased probability to suffer from hallmarks of neonatal sepsis, necrotizing enterocolitis, bronchopulmonary dysplasia and/or a disturbed microbiome development as described elsewhere herein by using the in vitro methods of the present invention. In particular, a method of evaluating the risk of a newborn subject for developing a NF-κB-associated postnatal inflammatory disorder or a postnatal alteration increasing the risk of a NF-κB-associated postnatal inflammatory disorder comprises determining the amount of S100A8/S100A9 heterodimer in a sample from said subject and comparing the result with a reference value as described elsewhere herein. In this regards the amount of S100A8/S100A9 heterodimer in a sample from said newborn subject is determined prior to the appearance of any hallmarks of a NF-κB-associated postnatal inflammatory disorder or a postnatal alteration increasing the risk of a NF-κB-associated postnatal inflammatory disorder. Hence, conclusions can be drawn before any postnatal treatment of a newborn subject with a medicament such as an antibiotic treatment in order to prevent a NF-κB-associated postnatal inflammatory disorder or a postnatal alteration increasing the risk of a NF-κB-associated postnatal inflammatory disorder. Moreover, evaluating the risk of a newborn subject for developing a NF-κB-associated postnatal inflammatory disorder or a NF-κB-associated postnatal alteration increasing the risk of a NF-κB-associated postnatal inflammatory disorder may help an attending physician to obtain the appropriate information to set the appropriate therapy conditions in case the S100A8/S100A9 level is increased as compared to a reference value or is above a defined threshold value. Preferably, the amount of S100A8/S100A9 heterodimer in a sample from said newborn subject is determined directly after birth. "Directly after birth" as used in this context means that the amount of S100A8/S100A9 heterodimer in a sample from said newborn subject is determined within the postnatal phase.

The term "postnatal" or "postnatal phase" as used according to the present invention means that the amount of S100A8/S100A9 heterodimer in a sample from said newborn subject is determined within the first hours, days, weeks or month of life. Preferably, the term "postnatal" as used herein means that the NF-κB-associated postnatal inflammatory disorder appears within the first month of life, more preferably within the first week of life. In this regard it is envisaged that the amount of S100A8/S100A9 heterodimer in a sample from said newborn subject is determined within 3, 5, 8, 10, 12, 18, 24, or 72 hours of life or within the first 4, 5, 6, 7, 8, 10, 14, 21 or 28 days of life. Preferably the amount of S100A8/S100A9 heterodimer in a sample from said newborn subject is determined within the first 3 days of life. In this regard it is particularly envisaged to determine the amount of S100A8/S100A9 in the umbilical cord blood after birth.

As described herein, a method of evaluating the risk of a newborn subject for developing a NF-κB-associated postnatal inflammatory disorder or a postnatal alteration increasing the risk of a NF-κB-associated postnatal inflammatory disorder might be particularly useful when a newborn subject is a premature subject or a newborn subject with a very low birth weight. Further, the method of evaluating the risk of a newborn subject for developing a NF-κB-associated postnatal inflammatory disorder or a postnatal alteration increasing the risk of a NF-κB-associated postnatal inflammatory disorder might be particularly useful when a newborn subject is a newborn subject delivered by Caesarean section. As outlined before, premature subjects and newborn subjects with a very low birth weight are at high risk for perinatal mortality and morbidity caused inter alia by newborn sepsis, i.e. a bacterial infection of the blood, or other NF-κB-associated postnatal inflammatory disorders, which can be explained by the low S100A8/S100A9 cord blood level of said subjects (FIG. 8) and the related missing S100A8/S100A9-induced immune tolerance. Further, as shown by the present inventors, also newborn subjects delivered by Caesarean section exhibit very low S100A8/S100A9 serum levels (FIG. 9). Thus, premature subjects, newborn subjects with a very low birth weight as well as newborn subjects delivered by Caesarean section are at an increased risk for developing a NF-κB-associated postnatal inflammatory disorder or a postnatal alteration increasing the risk of a NF-κB-associated postnatal inflammatory disorder associated with a low S100A8/S100A9 level. Accordingly, the described methods may be particularly useful for said subjects.

The term "disease" or "disorder" as used herein refers to any impairment of the normal state of a living animal subject or one of its parts that interrupts or modifies the performance of vital functions that is typically manifested by distinguishing signs and symptoms. Thus, a "disease" or "disorder" refers to any physical state of a subject connected with incorrectly functioning organ, part, structure, or system of the body resulting from the effect of genetic or developmental errors, infection, poisons, nutritional deficiency or imbalance, toxicity, or unfavorable environmental factors, illness, sickness, or ailment. In context of the present invention, the described disease or disorder is a postnatal inflammatory disorder. As outlined herein, said postnatal inflammatory disorder is a NF-κB-associated inflammatory disorder.

The term "NF-κB-associated" when used herein refers to any postnatal inflammatory disorder involving an increased activation of NF-κB, such as TLR-induced inflammatory disorders. Generally, the increased activation of NF-κB subsequently induces pro-inflammatory cytokines and leads to a state of hyperinflammation. Consequently, as demonstrated by the present inventors, S100A8/S100A9-induced programming of phagocytes showed cross-tolerance to other TLR-induced inflammatory patterns which are also NF-κB-associated, especially to TLR2 (FIG. 5 and FIG. 6). Accordingly, the means and methods described herein for use of S100A8 or S100A9 homodimer or S100A8/S100A9 heterodimer directly after birth might be suitable to prevent or treat hyperinflammation and bacterial overgrowth in newborn subjects during gram-positive as well as gram-negative challenges. Thus, the means and methods described herein for use of S100A8 or S100A9 homodimer or S100A8/S100A9 heterodimer to prevent or treat NF-κB-associated postnatal inflammatory disorders in newborn subjects might be equally suitable for all TLR-mediated postnatal inflammatory disorders that induce pro-inflammatory via activation of NF-κB.

Thus, according to the present invention, said NF-κB-associated postnatal inflammatory disorder is preferably a systemic hyperinflammatory response syndrome. It is particularly envisaged that the NF-κB-associated postnatal inflammatory disorder as described herein is a TLR-mediated NF-κB-associated postnatal inflammatory disorder. Preferably, said NF-κB-associated postnatal inflammatory disorder is a TLR4- and/or TLR2-mediated postnatal inflammatory disorder. The term "TLR4-mediated" as used herein means that said disorder is directly associated with the postnatal activation of the LPS-receptor complex TLR4/MD2/CD which regulates inflammatory processes against conserved structures of pathogens (Pathogen Associated Molecular Patterns), in particular gram-negative bacteria. The term "TLR2-mediated" as used herein means that said disorder is directly associated with the postnatal activation of the TLR2 receptor which regulates inflammatory processes against conserved structures of pathogens (Pathogen Associated Molecular Patterns), in particular gram-positive bacteria. After activation, the TLR4 and TLR2 receptors lead to the activation of NF-κB, thereby inducing pro-inflammatory cytokines including TNFα, IL-1β, IL-8 and IL-6. Thus, "TLR4- and/or TLR2-mediated" postnatal inflammatory disorders are diseases connected with an increased activation of NF-κB and an increased release of pro-inflammatory cytokines.

The term "inflammatory disorder" as used herein means that said refers to the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. The classical signs of acute inflammation are calor, dolor, rubor, tumor (heat, pain, redness and swelling) and loss of function. Thus, a postnatal inflammatory disorder according to the present invention is a postnatal inflammatory disorder characterized by at least one of said hallmarks of inflammation. Inflammation is a generic response, and therefore it is considered as a mechanism of innate immunity, as compared to adaptive immunity, which is specific for each pathogen. According to the present invention, the inflammatory disorder is a NF-κB-associated postnatal inflammatory disorder, such as a TLR4- and/or TLR2-mediated postnatal inflammatory disorder.

Preferably, the NF-κB-associated postnatal inflammatory disorder as described herein is an acute NF-κB-associated postnatal inflammatory disorder. An acute inflammation in this regard is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue. Preferably the NF-κB-associated postnatal inflammatory disorder is one of sepsis, necrotizing enterocolitis, and bronchopulmonary dysplasia. In this context it is envisaged that the NF-κB-associated inflammatory disorder appears "postnatal", i.e. within the first month of life, preferably within the first week of life as described elsewhere herein.

According to the present invention it is further envisaged that said sepsis is an early onset sepsis or a late onset sepsis. The term "early onset" as used herein refers to a sepsis developed between the first and the third day of life. The term "late onset" as used herein refers to a sepsis developed after the third day of life. Although the symptoms/signs of an early onset sepsis and a late onset sepsis can be nonspecific, the sepsis according to the present invention is preferably characterized by at least one clinical symptom selected from the group consisting of apnea, bradycardia, desaturation, instability of body temperature and feeding intolerance, and/or the presence of at least three of the following characteristics within 48 hours after onset of said clinical symptom(s): (a) C reactive protein (CRP) value higher than 20 mg/l, (b) hematologic abnormalities such as thrombocytopenia with a platelet count lower than 100,000/mm3, (c) neutropenia with an absolute neutrophil count lower than 2000/mm3, (d) left shift of segmented neutrophils with a ratio of immature to total neutrophils of 0.18 or higher, (e) radiographic evidence of pneumonia, (f) cultural evidence of infection, (g) green amniotic fluid, (h) premature rupture of membranes, and (i) signs of infection of the mother.

According to the present invention, S100A8 or S100A9 homodimer or S100A8/S100A9 heterodimer can further be used in the prevention or treatment of a NF-κB-associated postnatal inflammatory disorder in a newborn subject, wherein said NF-κB-associated postnatal inflammatory disorder in a newborn subject is preferably necrotizing enterocolitis. Said necrotizing enterocolitis is preferably characterized by at least one of the following symptoms: (a) bloody mucoid stools, (b) abdominal distension, (c) emesis, (d) radiographic evidence of pneumatosis intestinalis, (e) portal venous gas, (f) hematologic abnormalities, (g) thrombocytopenia with a platelet count lower than 100,000/mm3, (h) neutropenia with an absolute neutrophil count lower than 2000/mm3, and (i) left shift of segmented neutrophils with a ratio of immature to total neutrophils of 0.18 or higher.

According to the present invention it is further envisaged that said bronchopulmonary dysplasia is characterized by at least one of the following symptoms: (a) need of oxygen therapy, and (b) susceptibility to infection. Bronchopulmonary dysplasia is very common in infants with low birth weight and those who receive prolonged mechanical ventilation to treat respiratory distress syndrome (RDS). Further symptoms of bronchopulmonary dysplasia are for example a rapid, shallow breathing, a sharp pulling in of the chest below and between the ribs with each breath, grunting sounds and flaring of the nostrils.

The postnatal alteration increasing the risk of a NF-κB-associated postnatal inflammatory disorder in a newborn subject in the context of the present invention refers to any postnatal physiological change in the newborn subject that can cause a NF-κB-associated postnatal inflammatory disorder. The terms "increasing the risk of a NF-κB-associated postnatal inflammatory disorder" and "causing a NF-κB-associated postnatal inflammatory disorder" as used in this regard refers to the fact that said postnatal alteration which is not considered as postnatal disorder or disease can however in a newborn subject promote or facilitate occurrence of a NF-κB-associated postnatal inflammatory disorder. Generally, such postnatal alterations—in contrary to postnatal inflammatory disorders—do not automatically involve the immune system, but however lead to pathological postnatal development of immunity. Moreover, said pathological postnatal state caused by said postnatal alteration in a newborn subject increases the risk of a NF-κB-associated postnatal inflammatory disorder, such as a TLR4- and/or TLR2-mediated postnatal inflammatory disorder. In this context it is envisaged that said postnatal alteration increasing the risk of a NF-κB-associated postnatal inflammatory disorder appears within the first month of life, preferably within the first week of life. Preferably, said postnatal alteration increasing the risk of a NF-κB-associated postnatal inflammatory disorder in a newborn subject referred to herein is a disturbed microbiome development in a newborn subject. Equally envisaged are physiological changes affecting circulation and breathing, such as heart failure and respiratory, which are considered to influence development of NF-κB-associated postnatal inflammatory disorders.

Disturbed microbiome development in a newborn subject as described herein is a postnatal alteration preferably characterized by a decreased germ profile as compared to a newborn subject having a normal microbiome development. The human microbiome is composed of the microbes, as well as their genes and genomes, that live in and on the human body. Scientists are discovering just how important these resident microbes are to our health and well-being, particularly with respect to the roles they play in maintaining our immune systems, contributing to the digestion of our food, and acting as a first line of defense against pathogens. As reported in the art, there are many diseases in particular in newborn subjects that may be the result of a disturbed microbiome development (Matamoros et al., Trends Microbiol. (2013) 21(4):167-73). Moreover, because of said decreased germ profile, said disturbed microbiome development can increase the risk of a NF-κB-associated postnatal inflammatory disorder due to the insufficient microbe colonization of said newborn subject. In this respect, treatment of a newborn subject with S100A8 or S100A9 homodimer or S100A8/S100A9 heterodimer promotes microbiome development and eubiosis, by inducing immune tolerance towards colonizing microorganisms. According to the present invention, said disturbed microbiome development is a disturbed intestinal microbiome development, a disturbed respiratory microbiome development and/or a disturbed cutaneous microbiome development.

The term "subject" as used herein, also addressed as an individual, refers to a mammal organism, including a human or a non-human animal. Thus, the methods, uses and compositions described herein are generally applicable to both human and non-human mammals. A non-human animal may also represent a model of a particular disease or disorder. Alternatively, a non-human animal may represent a domesticated pet and/or livestock in need of treatment of a disease (for example a dog, cat, goat, bovine, ovine, etc.). Preferably, the subject of the present invention is a mammalian subject, in particular a human, a non-human primate, a dog, a horse, a cat, a guinea pig, a rabbit, a rat or a mouse. According to the present invention said subject is a newborn subject. The term "newborn subject" as used herein means that the subject is in the first four weeks after birth. More preferably, the newborn subject is in the first two weeks, more preferably still in the first week after birth. Thus, the newborn subject of the present invention is in the so called "postnatal phase" as defined elsewhere herein. As outlined elsewhere herein, a sample may be analyzed that has been obtained from said newborn subject, which is typically a living organism. Where the subject is a living human who may receive treatment for a disease or disorder as described herein, it is also addressed as a "patient".

Preferably, the newborn subject as described herein is a premature subject or a newborn subject delivered by Caesarean section. As known in the art, premature infants are at much higher risk of developing postnatal sepsis than are infants born at full term. The terms "premature" or ""preterm" as used herein means that said newborn subject is born untimely, i.e. before the general gestation age of about 40 weeks. According to the present invention, the premature newborn subject is a newborn subject born with a gestation age of less than 37 weeks, preferably with a gestation age of less than 36, 35, 34, 33, 32, or 31 weeks. More preferably, the premature newborn subject of the present invention is born with a gestation age of less than 30 weeks. Most preferably, the premature newborn subject of the present invention is born with a gestation age of less than 28 weeks. The term "delivered by Caesarean section", also known as C-section, refers to the use of surgery to give birth to one or more mammalian subjects. A Caesarean section is often performed when a vaginal delivery would put the fetus or the mother at risk. This may include obstructed labour, twin pregnancy, high blood pressure in the mother, breech birth, problems with the placenta, umbilical cord or shape of the pelvis, and previous C-section. As discovered by the present inventors, premature human subjects as well as human newborn subjects delivered by Caesarean section exhibit a significantly lower S100A8/S100A9 level than full term human newborn subject or vaginally delivered human subjects (FIG. 8 and FIG. 9). Further, a massively high concentration of S100A8/S100A9 derivatives could be detected in breast milk (FIG. 10). Thus, without being bond by theory, the present inventors suggest that these observations possibly describes an overriding principle to prevent extreme inflammatory reactions on postnatal bacterial settlements of newborn subjects, in particular premature subjects and newborn subjects delivered by Caesarean section which are characterized by an altered bacterial colonization due to the particular circumstances of birth. Thus, the present invention describes in this connection the possibility of a preventive or therapeutic use of endogenous alarmins such as S100A8/S100A9 derivatives against the formation of a NF-κB-associated postnatal inflammatory disorders or postnatal alteration increasing the risk of a NF-κB-associated postnatal inflammatory disorder.

In this respect the use of S100A8 or S100A9 homodimer or S100A8/A9 heterodimer in the prevention or treatment of a NF-κB-associated postnatal inflammatory disorders or postnatal alterations increasing the risk of a NF-κB-associated postnatal inflammatory disorder in a newborn subject preferably induces microbial hyporesponsivity of myeloid cells in said subject. The term "microbial hyporesponsivity" means that the substitutions by S100A8 or S100A9 homodimer or S100A8/A9 heterodimer induces a tolerant state of hyporesponsiveness to LPS, thereby preventing NF-κB-associated hyperinflammatory responses of said myeloid cells and thus postnatal TLR-mediated inflammatory disorders or postnatal disorders alterations increasing the risk of a NF-κB-associated postnatal inflammatory disorder. Accordingly, within the scope of the present invention it is envisaged that the S100A8 or S100A9 homodimer or the S100A8/A9 heterodimer as described herein induces immune and stress tolerance. Preferably, the induced effect is dose- and time-dependent. As firstly demonstrated by the present inventors, a substitution with S100A8 or S100A9 homodimers and S100A8/A100A9 heterodimers in an endotoxin (LPS administration) model as well as a staphylococcus/sepsis model of S100-knock-out mice leads to a significantly elevated survival rate of said animals. In this regard the induced effect is a dose- and time-dependent establishment of microbial hyporesponsiveness leading to the significantly increased survival rate of said subjects (FIG. 5 and FIG. 6).

For the induced effect of S100A8 or S100A9 homodimers and S100A8/A100A9 heterodimers in the prevention of a NF-κB-associated postnatal inflammatory disorder or a postnatal alteration increasing the risk of a NF-κB-associated postnatal inflammatory disorder in a newborn subject it is further envisaged that the newborn subject is treated with said S100A8 or S100A9 homodimer or said S100A8/A9 heterodimer for at least 12, 24, 36, 48 or 72 hours, or at least 4, 5, 6, or 7 days after birth. Preferably, the newborn subject it treated with said S100A8 or S100A9 homodimer or said S100A8/A9 heterodimer for at least 24 hours after birth.

According to the present invention, the administration of a S100A8 or S100A9 homodimer or S100A8/A9 heterodimer for use in the prevention or treatment of a NF-κB-associated postnatal inflammatory disorders or postnatal alterations increasing the risk of a NF-κB-associated postnatal inflammatory disease can be carried out by any method known in the art. Preferably, said S100A8 or S100A9 homodimer or said S100A8/A9 heterodimer can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, or by combinations thereof. In this regard it is envisaged that said S100A8 or S100A9 homodimer or said S100A8/A9 heterodimer is orally administered with the nutrient. According to the present inventors, there is no limitation for the recombinant production of S100A8 or S100A9 homodimers or S100A8/A9 heterodimers and both homodimers and heterodimers are very stable, can be stably stored over a wide pH range (2-9), are temperature insensitive, and insensitive to light. Thus, both a systemic and oral pharmacological application of S100A8 or S100A9 homodimers or S100A8/A9 heterodimers is envisaged according to the present invention, which makes these protein complexes very attractive for pharmacological and medical application.

Accordingly, in another aspect, the present invention also relates to a pharmaceutical composition comprising S100A8 or S100A9 homodimer or S100A8/A9 heterodimer for use in the prevention or treatment of a NF-κB-associated postnatal inflammatory disorder or a postnatal alteration increasing the risk of a NF-κB-associated postnatal inflammatory disorder in a newborn subject. Equally, in another aspect, the present invention refers to a method for the prevention or treatment of a NF-κB-associated postnatal inflammatory disorder or a postnatal alteration increasing the risk of a NF-κB-associated postnatal inflammatory disorder in a newborn subject, said method comprising administering a therapeutically effective amount of S100A8 or S100A9 homodimer or S100A8/A9 heterodimer to the subject in need thereof. Further, in another aspect, the present invention provides for the use of S100A8 or S100A9 homodimer or S100A8/A9 heterodimer for the preparation of a medicament for the prevention or treatment of a NF-κB-associated postnatal inflammatory disorder or a postnatal alteration increasing the risk of a NF-κB-associated postnatal inflammatory disorder in a newborn subject. Accordingly, the methods and uses described herein comprise administering to a subject, in particular a newborn subject in need thereof a S100A8 or S100A9 homodimer or S100A8/S100A9 heterodimer. Thus, the S100A8 or S100A9 homodimer or S100A8/S100A9 heterodimer may be administered in the form of a pharmaceutical composition, as defined elsewhere herein. Preferably, the S100A8 or S100A9 homodimer or S100A8/S100A9 heterodimer are administered in a therapeutically effective amount.

The term "therapeutically effective amount" as used herein is understood as a sufficient amount of S100A8 or S100A9 homodimer or S100A8/S100A9 heterodimer to prevent or treat a NF-κB-associated postnatal inflammatory disorder or to prevent or treat a postnatal alteration increasing the risk of a NF-κB-associated postnatal inflammatory disorder, i.e. the reasonable benefit/risk ratio applicable to any medical treatment. Thus, said therapeutically effective amount should be sufficient to inhibit or alleviate the symptoms of a NF-κB-associated postnatal inflammatory disorder or a postnatal alteration increasing the risk of a NFκB-associated postnatal inflammatory disorder. By "therapeutic effect" or "therapeutically effective" is meant that the compounds for use will elicit the biological or medical response of a tissue, system, animal or human that is being sought by the researcher, veterinarian, medical doctor or other clinician. The term "therapeutically effective" further refers to the inhibition of factors causing or contributing to the disease or disorder. The term "therapeutically effective amount" includes that the amount of the compound when administered is sufficient to significantly improve the progression of the disease or disorder being treated or to prevent development of said disease or disorder. The therapeutically effective amount will vary depending on the compound, the disorder and its severity and on individual factor of the subject such. Therefore, as said before, the compounds of the present invention will not in all cases turn out to be therapeutically effective, because the method disclosed herein cannot provide a 100% safe prediction whether or not a subject may be responsive to said compound, since individual factors are involved as well. It is to expect that age, body weight, general health, sex, diet, drug interaction and the like may have a general influence as to whether or not the compound for use in the treatment of a newborn subject suffering or being at the risk to suffer from a NF-κB-associated postnatal inflammatory disorder or a postnatal alteration increasing the risk of a NF-κB-associated postnatal inflammatory disorder will be therapeutically effective.

Preferably, the therapeutically effective amount of the compound used to treat a subject suffering or being at the risk to suffer from a NF-κB-associated postnatal inflammatory disorder or a postnatal alteration increasing the risk of a NF-κB-associated postnatal inflammatory is between about 0.001 mg per kg body weight and about 1 g per kg body weight, such as about 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 100, 200, 300, 400, 500, 600, 700, 800, or about 900 mg per kg body weight. Even more preferably, the therapeutically effective amount of the S100A8 homodimer or the S100A9 homodimer used to treat a subject suffering or being at the risk to suffer from a NF-κB-associated postnatal inflammatory disorder or a postnatal alteration increasing the risk of a NF-κB-associated postnatal inflammatory is between about 0.001 mg per kg body weight and about 100 mg per kg body weight, such as between about 0.01 mg per kg body weight and about 50 mg per kg body weight, in particular between 2.5 and 5 mg per kg body weight. Preferably, the therapeutically effective amount of the S100A8/S100A9 heterodimer used to treat a subject suffering or being at the risk to suffer from a NF-κB-associated postnatal inflammatory disorder or a postnatal alteration increasing the risk of a NF-κB-associated postnatal inflammatory is between about 0.001 mg per kg body weight and about 100 mg per kg body weight, such as between about 0.01 mg per kg body weight and about 100 mg per kg body weight, in particular between 25 and 50 mg per kg body weight. The therapeutic effective amount of the compound will vary with regard to the weight of active compound contained therein, depending on the species of subject to be treated.

It will be understood that the total daily dosage of the compounds of the present invention will be decided by the attending physician within the scope of medical judgment. The specific therapeutically effective dose level for any particular patient will depend upon a variety of factors including the disorder being prevented or treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidental with the specific polypeptide employed, and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.001 to 1,000 mg per kg per day. The daily dose of the S100A8 or S100A9 homodimer may be varied over a range from 0.001 to 10 mg per kg per day. The daily dose of the S100A8/S100A9 heterodimer may be varied over a range from 0.001 to 100 mg per kg per day. The S100A8 or S100A9 homodimer or S100A8/S100A9 heterodimer to be administered may be combined with pharmaceutically acceptable excipients, and optionally sustained-release matrices, such as biodegradable polymers, to form therapeutic compositions.

The compositions according to the present invention are preferably formulated in a unit dosage form, each dosage containing about 1 to about 500 mg, more usually about 5 to about 300 mg, of the active ingredient. The term "unit dosage form" as used herein refers to physically discreet units suitable as unitary dosages for human subjects or other mammals, each unit containing a predetermined quantity of active material calculated to produce the desired therapeutic effect, in association with a suitable pharmaceutical carrier. As used herein, a "dosage" refers to an amount of therapeutic agent administered to a patient. As used herein, a "daily dosage" refers to the total amount of therapeutic agent administered to a patient in a day.

Pharmaceutically acceptable excipients according to the present invention include, by the way of illustration and not limitation, diluent, disintegrants, binding agents, adhesives, wetting agents, polymers, lubricants, gliands, substances added to mask or counteract a disagreeable texture, taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The diagnostic compositions can additionally include preservatives, solubilizers, stabilizers, wetting agents, emulsifiers, sweeteners, colorants, flavorings, buffers, coating agents, or antioxidants. Suitable diagnostic carriers are described in Remington's Pharmaceutical Sciences, Mack Publishing Company, a standard reference text in this field.

In the pharmaceutical compositions of the present invention, the active principle, i.e. the S100A8 or S100A9 homodimer or S100A8/S100A9 heterodimer alone or in combination with another active principle, can be administered in a unit administration form, as a mixture with conventional pharmaceutical supports, to the newborn subject of the present invention. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles that are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions, formulations including sesame oil, peanut oil or aqueous propylene glycol, and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The S100A8 or S100A9 homodimer or S100A8/S100A9 heterodimer of the present invention can also be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. In addition the S100A8 or S100A9 homodimers or S100A8/S100A9 heterodimers of the invention formulated for parenteral administration, such as intravenous or intramuscular injection, other pharmaceutically acceptable forms include, e.g. tablets or other solids for oral administration, liposomal formulations, time release capsules, and any other form currently used.

Further, pharmaceutical compositions of the present invention may comprise an additional therapeutic active agent such as anti-inflammatory drugs, antibiotics or immunoglobulins neutralizing bacterial toxins. Thus, the S100A8 or S100A9 homodimer or S100A8/S100A9 heterodimer of the present invention may also be used in combination with other therapeutically active agents. Preferred anti-inflammatory drugs in this regard are corticosteroids such as glucocorticoids. Preferred antibiotics in this respect are ampicillin, gentamicin, tobramycin, cefotaxom, vancomycin, meropenem, imipenem, linezolid, penicillin G, and metronidazole. Further, the S100A8 or S100A9 homodimer or S100A8/S100A9 heterodimer of the present invention may also be used in combination with antimycotics, such as fluconazole, amphotericin B, and nystatin. Thus, the S100A8 or S100A9 homodimer or S100A8/S100A9 heterodimer of the present invention may be intended to be administered separately from other therapeutically active agents. Alternatively, in the "combination" treatments described herein the S100A8 or S100A9 homodimer or S100A8/S100A9 heterodimer and the other therapeutically active agents are sequentially or simultaneously combined. Thus, the agents may be administered in individually varying dose schedules and via different routes. For example, when administered sequentially, the agents can be administered at closely spaced intervals (e.g., over a period of 5-10 minutes) or at longer intervals (e.g. 1, 2, 3, 4 or more hours apart, or even longer periods apart where required), the precise dosage regimen being commensurate with the properties of the therapeutic agent(s) as described herein, including their synergistic effect. The agents may be formulated together in a single dosage form, or alternatively, the individual agents may be formulated separately and presented together in the form of a kit (e.g. in blister packs) optionally with instructions for their use.

Accordingly, in another aspect, the present invention also relates to a kit-of-part that is suitable for use in the prevention or treatment of a NF-κB-associated postnatal inflammatory disorder or a postnatal alteration increasing the risk of a NF-κB-associated postnatal inflammatory disorder. In one embodiment, the kit-of-part of the invention may comprise (i) a S100A8 or S100A9 homodimer or a S100A8/

S100A9 heterodimer as defined elsewhere herein, and (ii) at least one anti-inflammatory drug, each of (i) and (ii) being laid out to be administered separately, sequentially or simultaneously. In one embodiment, the kit-of-part of the invention may comprise (i) a S100A8 or S100A9 homodimer or a S100A8/S100A9 heterodimer as defined elsewhere herein, and (ii) at least one antibiotic, each of (i) and (ii) being laid out to be administered separately, sequentially or simultaneously. In one embodiment, the kit-of-part of the invention may comprise (i) a S100A8 or S100A9 homodimer or a S100A8/S100A9 heterodimer as defined elsewhere herein, and (ii) at least one immunoglobulin neutralizing bacterial toxins, each of (i) and (ii) being laid out to be administered separately, sequentially or simultaneously. In one embodiment, the kit-of-part of the invention may comprise (i) a S100A8 or S100A9 homodimer or a S100A8/S100A9 heterodimer as defined elsewhere herein, and (ii) at least one anti-inflammatory drug, each of (i) and (ii) being laid out to be administered separately, sequentially or simultaneously.

S100A8 or S100A9 homodimers and S100A8/S100A9 heterodimers as disclosed herein may also be useful for the prevention or treatment of a NF-κB-associated postnatal inflammatory disorder or a postnatal alteration increasing the risk of a NF-κB-associated postnatal inflammatory disorder in domestic animals such as cats, dogs, rabbits, guinea pigs, cows, sheeps, and horses. Thus, the invention also provides a veterinary formulation comprising S100A8 or S100A9 homodimer or S100A87S100A9 heterodimer for use in the prevention or treatment of a NF-κB-associated postnatal inflammatory disorder or a postnatal alteration increasing the risk of a NF-κB-associated postnatal inflammatory disorder in a newborn subject together with a veterinary acceptable diluents or carrier. Such formulations include in particular ointments, pour-on formulations, spot-on formulations, dips, sprays, mousses, shampoos, collar, and powder formulations.

Unless otherwise stated, the following terms used in this document, including the description and claims, have the definitions given below.

Those skilled in the art will recognize, or be able to ascertain, using not more than routine experimentation, many equivalents to the specific embodiments of the invention described herein. Such equivalents are intended to be encompassed by the present invention.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "consisting", "consisting of" and "consisting essentially of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

As described herein, "preferred embodiment" means "preferred embodiment of the present invention". Likewise, as described herein, "various embodiments" and "another embodiment" means "various embodiments of the present invention" and "another embodiment of the present invention".

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

The description includes information that may be useful in understanding the present invention. It is not an admission that any of the information provided herein is prior art or relevant to the presently claimed inventions, or that any publication specifically or implicitly referenced is prior art.

EXAMPLES

The following examples illustrate the invention. These examples should not be construed as to limit the scope of this invention. The examples are included for purposes of illustration and the present invention is limited only by the claims. It will be clear to a skilled person in the art that the invention may be practiced in other ways than as particularly described in the present description and examples. Numerous modifications and variations of the present invention are possible in light of the above teachings and, therefore, are within the scope of the appended claims.

Figure 1:
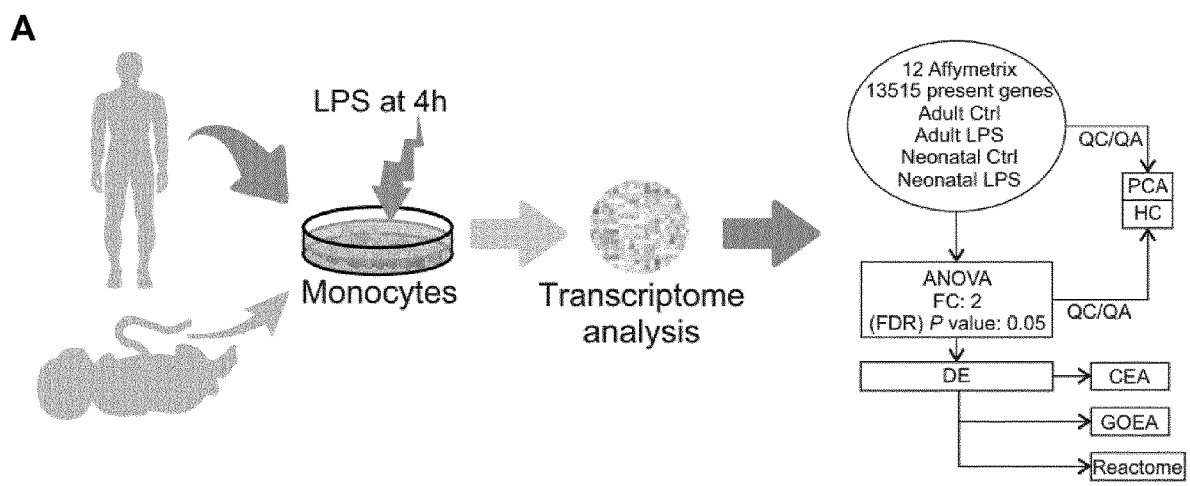
FIG. 1: LPS-induced transcriptomic changes in adult and neonatal monocytes. (A) Experimental setup and bioinformatic data analysis. QC/QA=quality control/quality assurance. (B) Visualization of expression differences of individual groups relative to the group mean on the CEA network. (C) Fold-changes of LPS-induced expression of selected MyD88- and TRIF-dependent genes (qRT-PCR). Bars represent mean±s.d. (n=7). *P<0.05, **P<0.005, Student's t-test.
Figure 1:
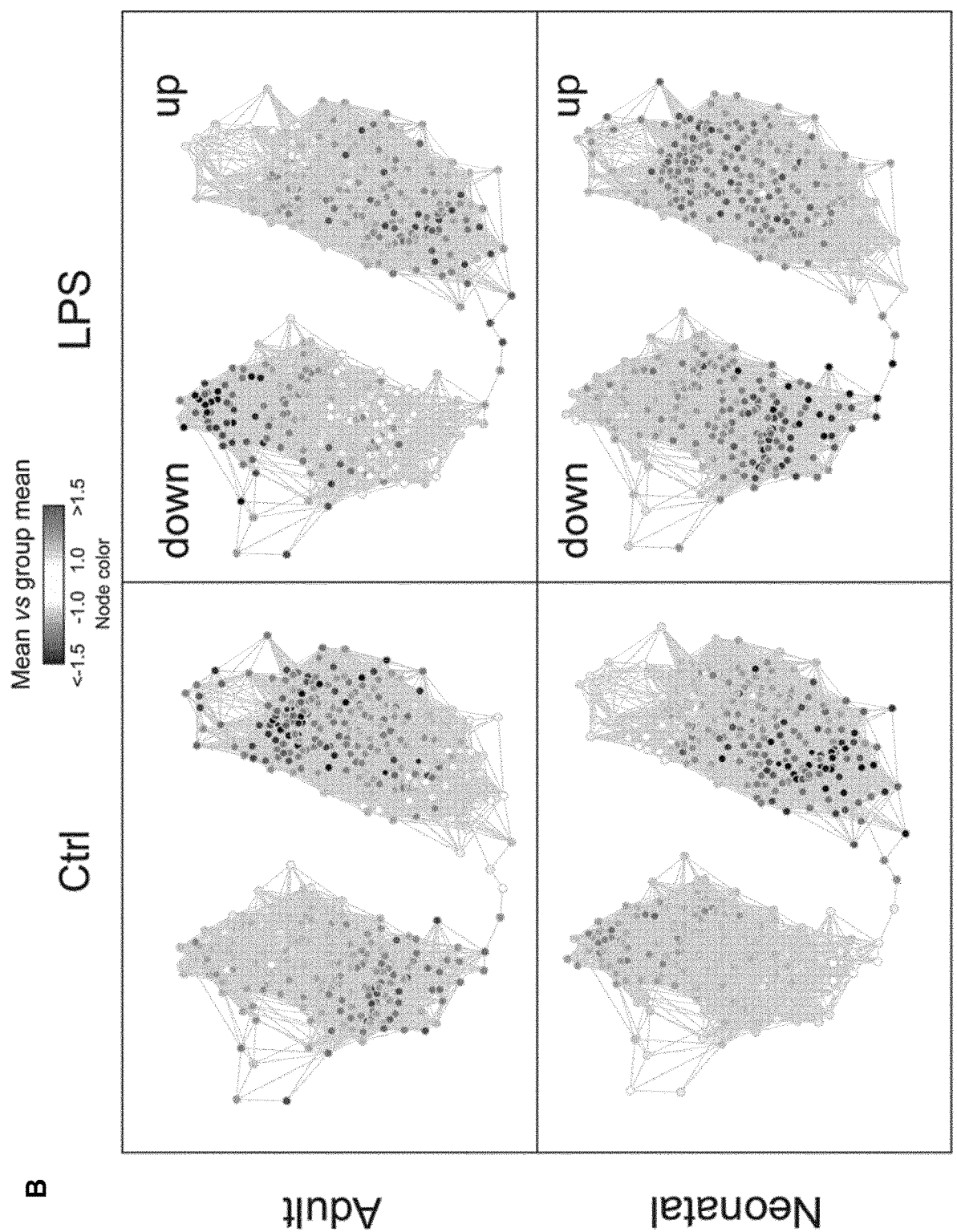
Figure 1:
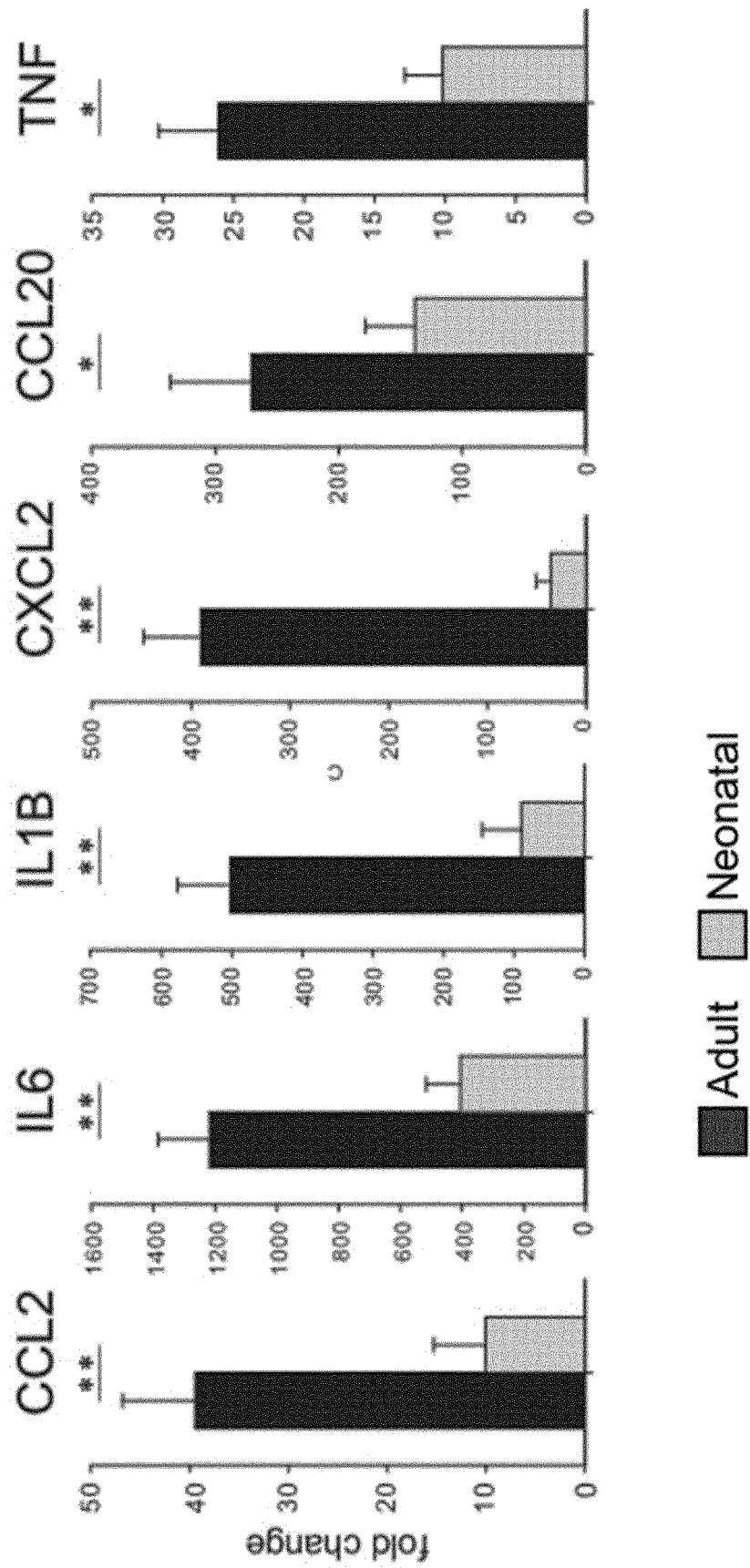
Figure 1:
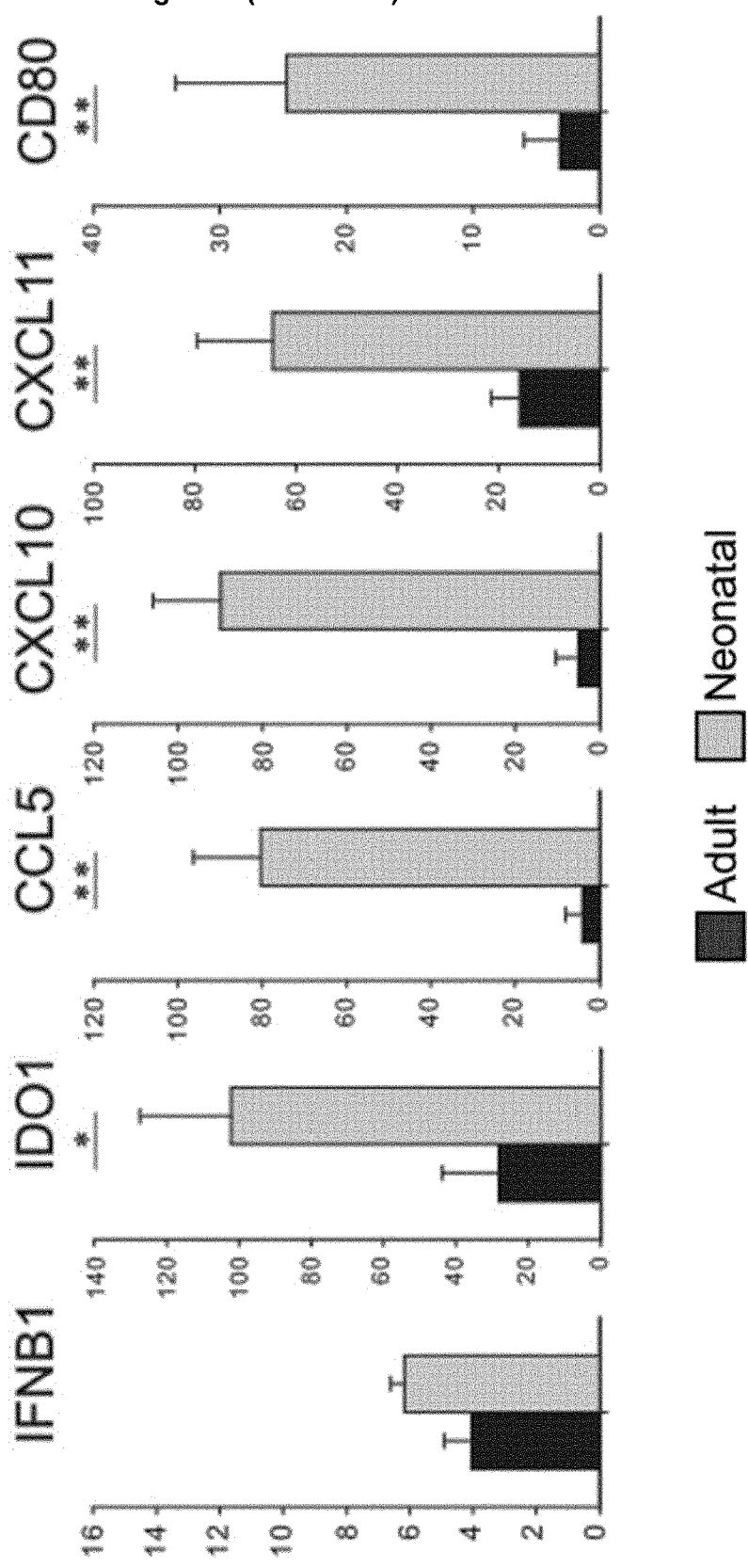

To capture the overall differences between newborns and adults, the present inventors assessed global transcriptional regulation in isolated adult blood (AB) and cord blood (CB) monocytes (Mo) in response to LPS stimulation (FIG. 1A). Here differentially expressed (DE) genes could be identified and co-expressed genes as a network could be visualized (FIG. 1B). Two major clusters evolved, reflecting genes up- (right cluster) or down-regulated (left cluster) by LPS (FIG. 1B). Within the clusters, the distribution of the most strongly regulated genes differed considerably between AB-Mo and CB-Mo. Clustering according to gene ontology annotations (GOEA) pointed to differential involvement of the main signalling signaling modules downstream of TLR4 (FIG. 2A and FIG. 2B), which was further validated by pathway enrichment analyses (data not shown). Gene up-regulation by LPS was mainly mediated through MyD88-dependent signaling in AB-Mo but primarily through TRIF-dependent signaling in CB-Mo. In independent experiments using quantitative PCR (qPCR), a significantly higher up-regulation of MyD88/NF-κB/IRF5-dependent candidate genes (CCL2, IL-6, IL-1β, CXCL2, CCL20, TNFα) after stimulation by LPS in AB-Mo could be demonstrated. In contrast, the induction of TRIF/IRF3/STAT1-dependent regulatory IFNγ response genes (IFNB1, IDO1, CCL5, CXCL10, CXCL11, CD80) was significantly higher in CB-Mo (FIG. 1D).

Figure 2:
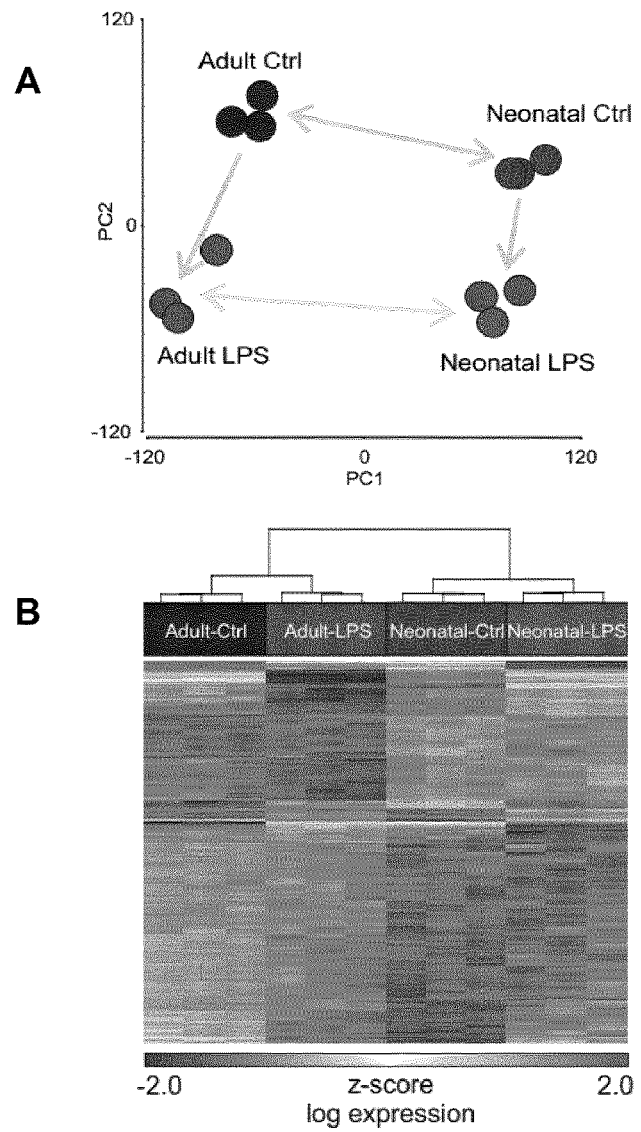
FIG. 2: Basic gene expression differences between adult and neonatal monocytes. (A) PCA of the transcriptome data depicting the group relationship of adult (AB-Mo) resp. neonatal (CB-Mo) Mo with (LPS) or without (Ctrl) LPS-treatment. (B) Hierarchical clustering of the 1.000 genes with the highest variance within the dataset (P<0.000005, one-way ANOVA). (C) Diagram indicating the numbers of differentially expressed (DE) genes. (D) GOEA of basal DE genes. (E) Relative basal expression of MyD88- and TRIF-dependent genes (qRT-PCR). Bars represent mean±s.d. (n=7). *P<0.05, **P<0.005, Student's t-test. (F) Left: DE genes at baseline and LPS-level plotted on the CEA network. Highlighted are genes loosing expression differences after LPS stimulation. Right: TF prediction analysis for DE genes at baseline. NES=normalized enrichment score.
Figure 2:
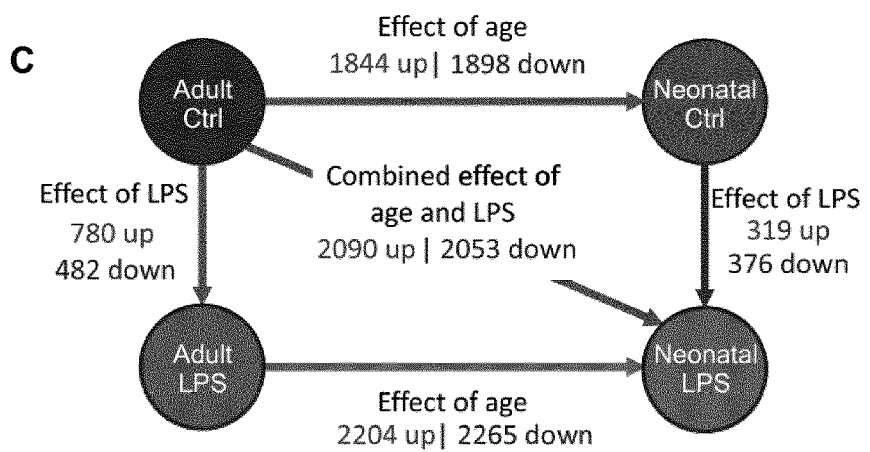
Figure 2:
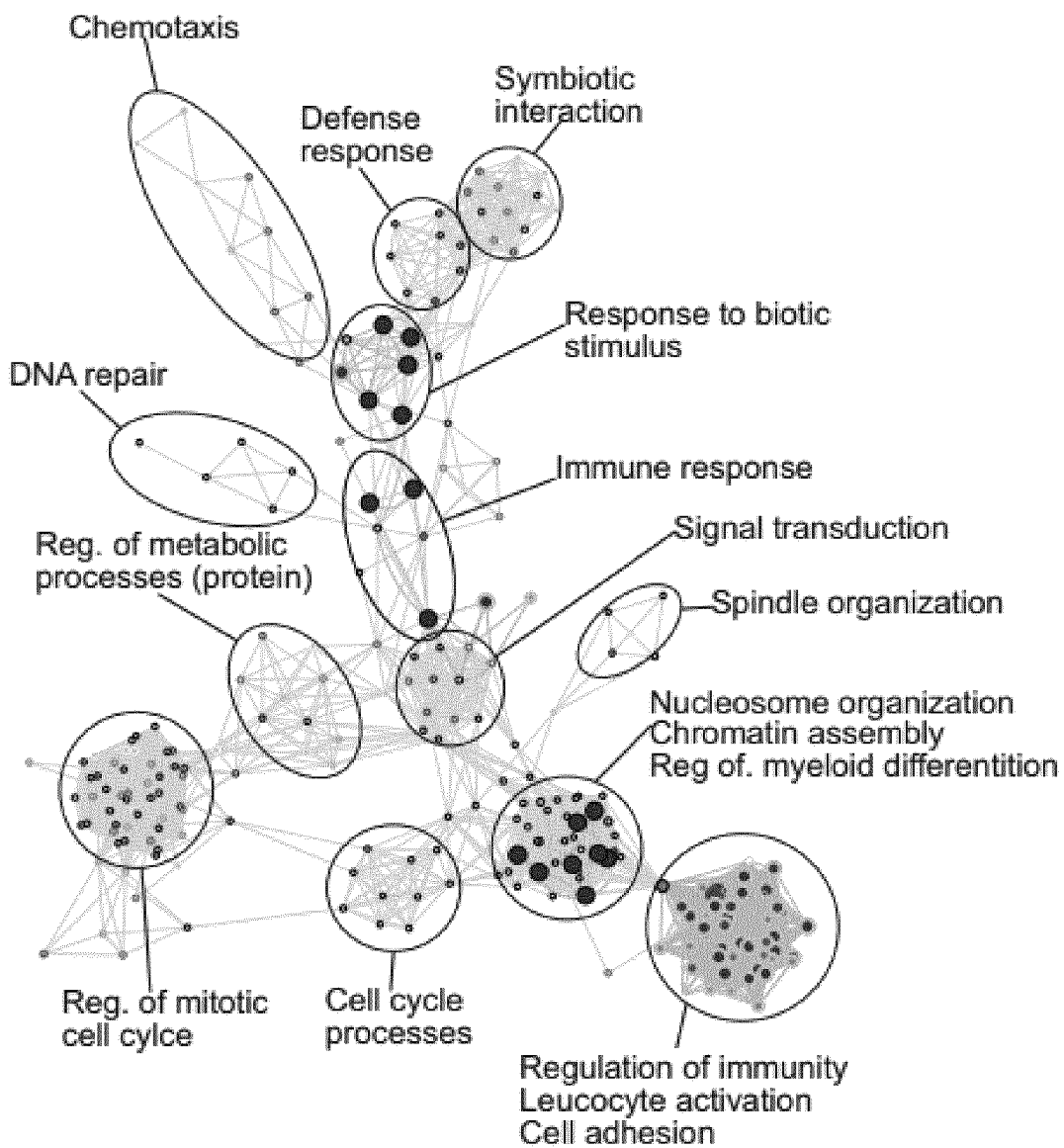
Figure 2:
Figure 2:
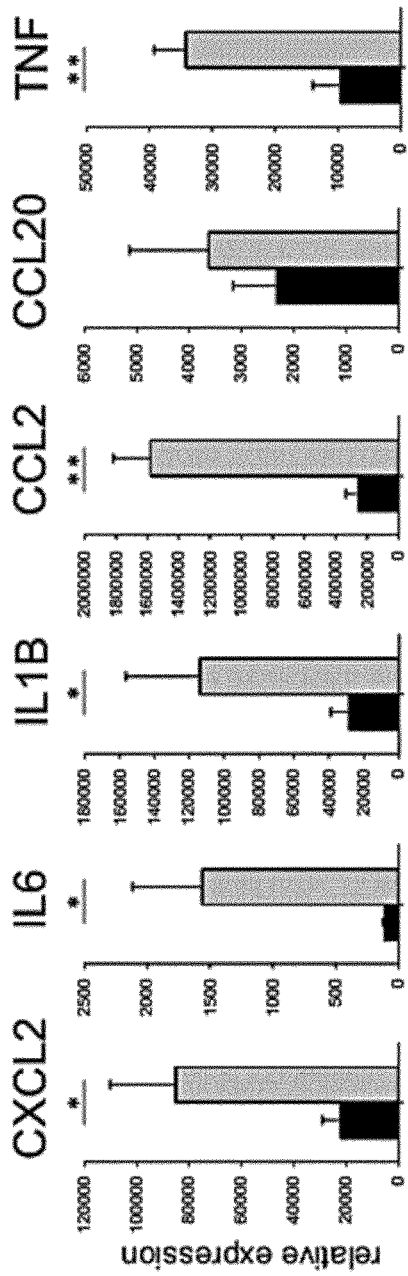
Figure 2:
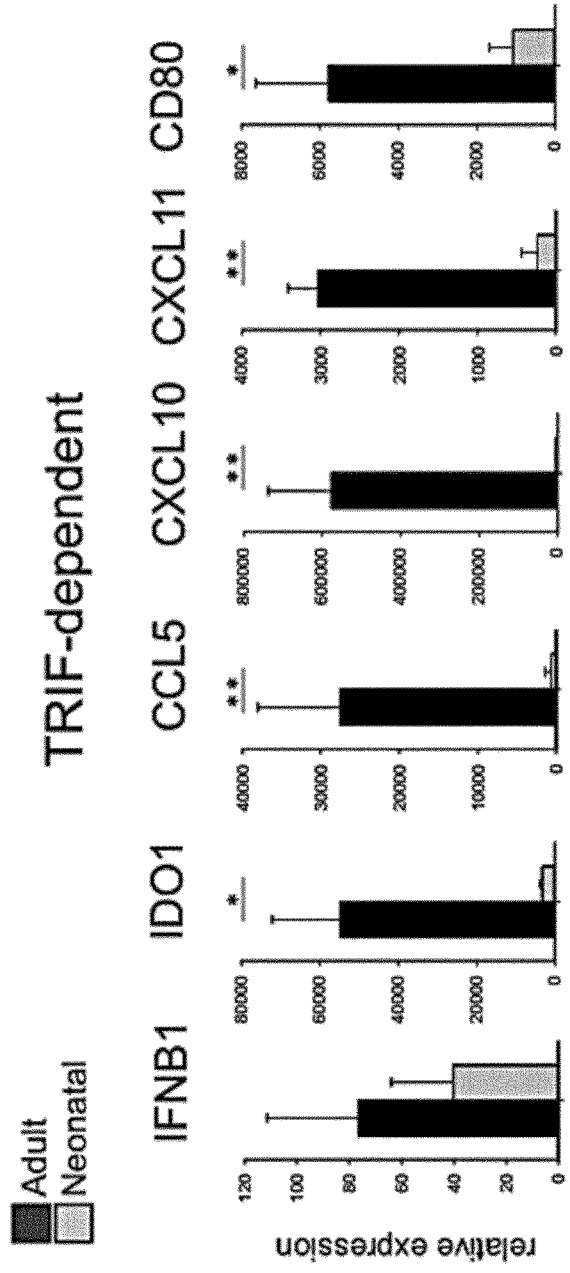
Figure 2:
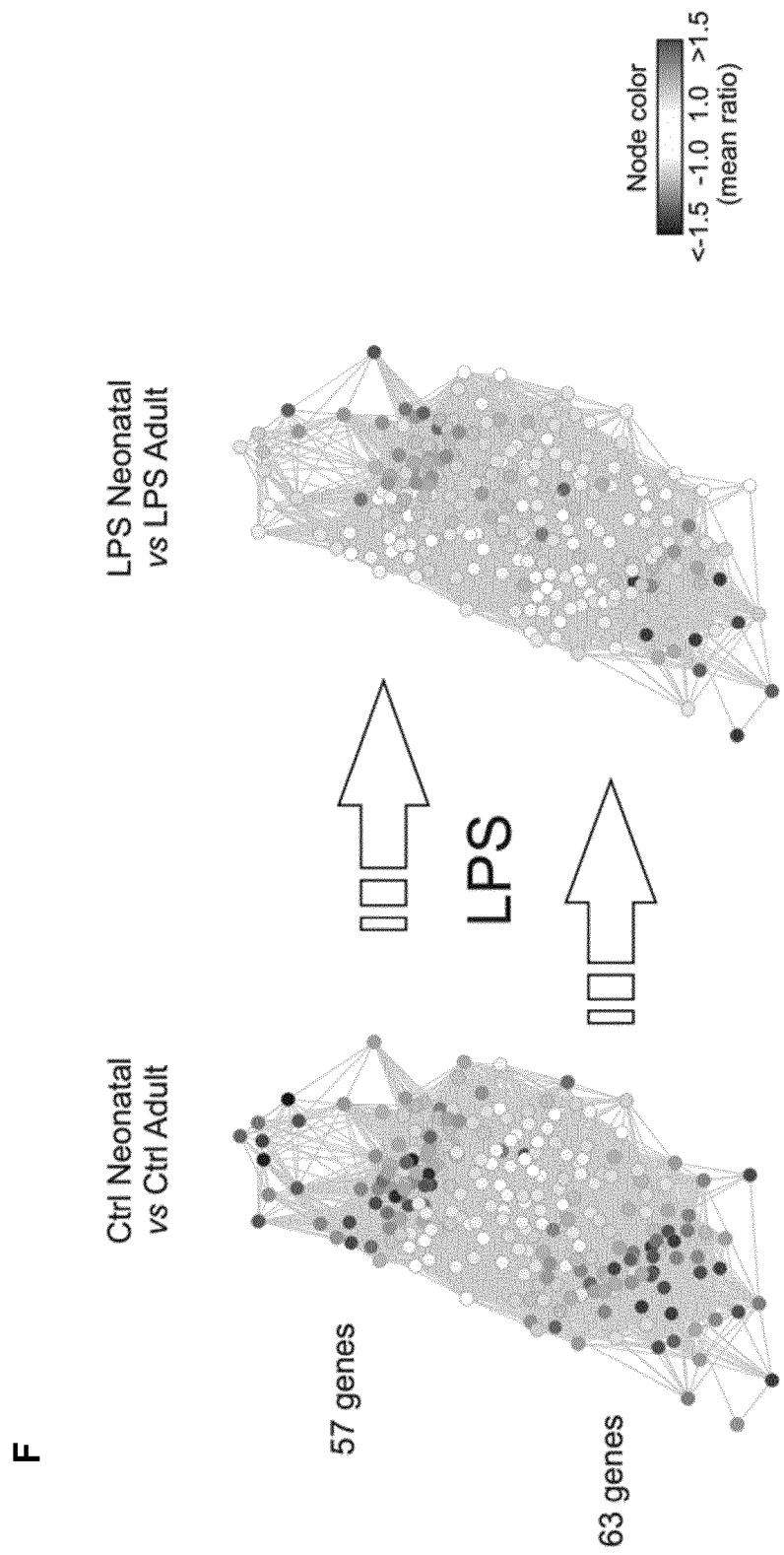
Figure 10:
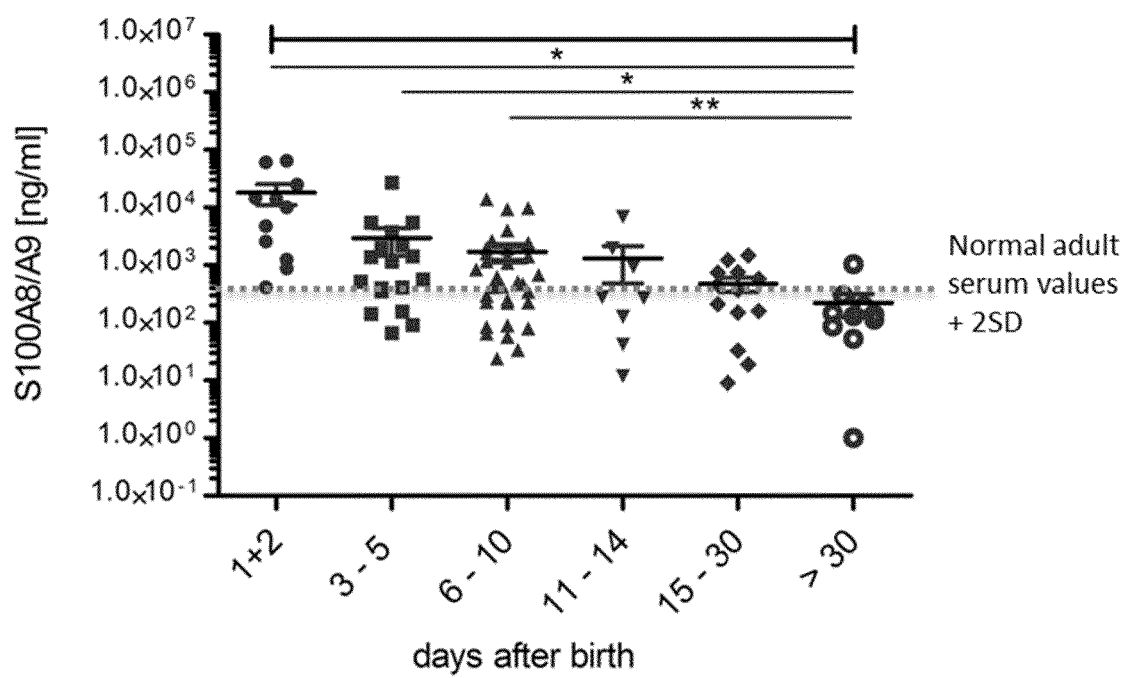
FIG. 10: S100A8/S100A9 concentration in human breast milk in dependence on the life of age of the newborn. Concentration of S100A8/S100A9 heterodimer in human breast mild is significantly elevated during the first month of life of the newborn compared to normal adult serum levels of S100A8/S100A9 heterodimer.

To better understand the reciprocal usage of defined TLR4 signaling modules in AB-Mo and CB-Mo a principal component analysis (PCA) (FIG. 2A) and hierarchical clustering (HC) of the 1,000 genes with the highest variance within the dataset (FIG. 2B) was performed. Surprisingly, baseline differences between AB-Mo and CB-Mo (Extended Data Table 3) turned out to be more pronounced than the expression changes induced by LPS. The highest number of DE genes was found between AB-Mo and CB-Mo at baseline (FIG. 2C) suggesting that differences in the response towards LPS are primarily determined by baseline differences. GOEA (FIG. 2D) and HC (data not shown) of basal DE genes indicated that genes with elevated basal expression in CB-Mo had pro-inflammatory immune response functions, whereas genes associated with immunoregulation were lower expressed compared to AB-Mo. Independent qPCRs proved that pro-inflammatory MyD88-dependent genes were basal elevated in CB-Mo while TRIF-dependent regulatory genes were barely expressed compared to AB-Mo (FIG. 2E). Basal expression level obviously affected inversely the LPS responsivity (FIG. 10). This inverse relation also held true when using an unbiased approach analyzing co-expression networks of LPS-inducible genes (FIG. 2F). At baseline, 63 co-expressed genes were higher expressed in CB-Mo but increased less upon LPS stimulation than in AB-Mo, so expression differences decreased at the LPS-level. In contrast, 57 basal lower expressed genes in CB-Mo responded with higher LPS-induced fold-changes reaching comparable LPS-induced expression level as in AB-Mo.

Using these two gene groups as a bait, overrepresentation analyses revealed a strong enrichment of IRF3 transcription factor binding sites (TFBS) and STAT1-TFBS for the 57 low expressed genes, while the 63 genes elevated in CB-Mo were primarily NF-κB targets (FIG. 2F). Unbiased TFBS overrepresentation analyses using the top 2.5% of genes contributing to the first and second principal component of the PCA yielded similar results (data not shown). LPS-induced transcriptomic shifts of AB-Mo and CB-Mo likewise had NF-κB-TFBS significantly enriched, whereas the basic shift between AB-Mo and CB-Mo was characterized by a significant enrichment of IFR5-TFBS and underrepresentation of STAT1-TFBS in neonatal transcriptomes. Summarized, these data suggested high NF-κB/IRF5 and low IRF3/STAT1 activity in neonatal Mo at baseline, the latter being in line with a recent in silico study of Mo expression data that proposed deficient IRF3 activity in neonates (Lissner M. M. et al. PLoS One (2015) 10, e0132061). Interestingly, in preterms, 70 IFN response genes downstream of the TRIF-axis were shown to be expressed at even lower levels than in term newborns (Singh V. V. et al. PLoS One (2013) 8, e62845).

Figure 3:
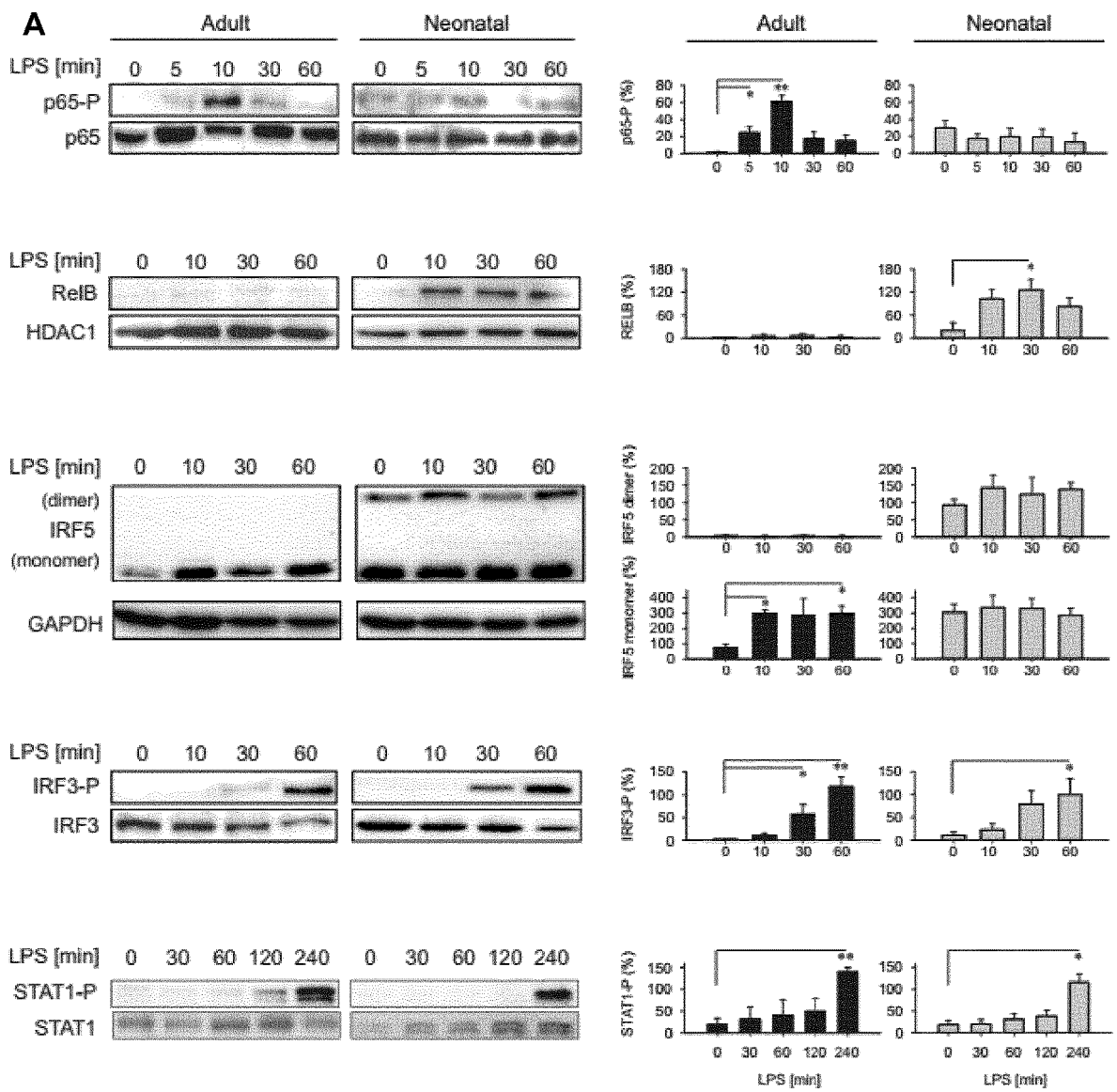
FIG. 3: Transcriptional regulation of LPS response genes in adult and neonatal monocytes. (A) Representative immunoblots of LPS-activated p65-P, RelB, IRF5, IRF3-P, and STAT1-P. Densitometric data represent mean percentages of respective loading controls±s.d. (n=4). *P<0.05, **P<0.005, Student's t-test. (B) Relative expression of MyD88- and TRIF-dependent genes in CB-Mo after indicated culture times in the absence and presence of S100A8/S100A9. Bars represent mean±s.d. (n=3) *P<0.05, Student's t-test. (C) S100A8/S100A9-induced TF activation in AB-Mo. Representative blots and densitometry (n=3). *P<0.05, **P<0.005, Student's t-test. (D) Representative PCRs of indicated gene promoters from n=5 independent ChIP assays. (E) Quantitative analysis of the ChIP-PCRs by densitometry, plotted as mean percentages from input (IP; 100%)±s.d. *P<0.05, Student's t-test.
Figure 3:
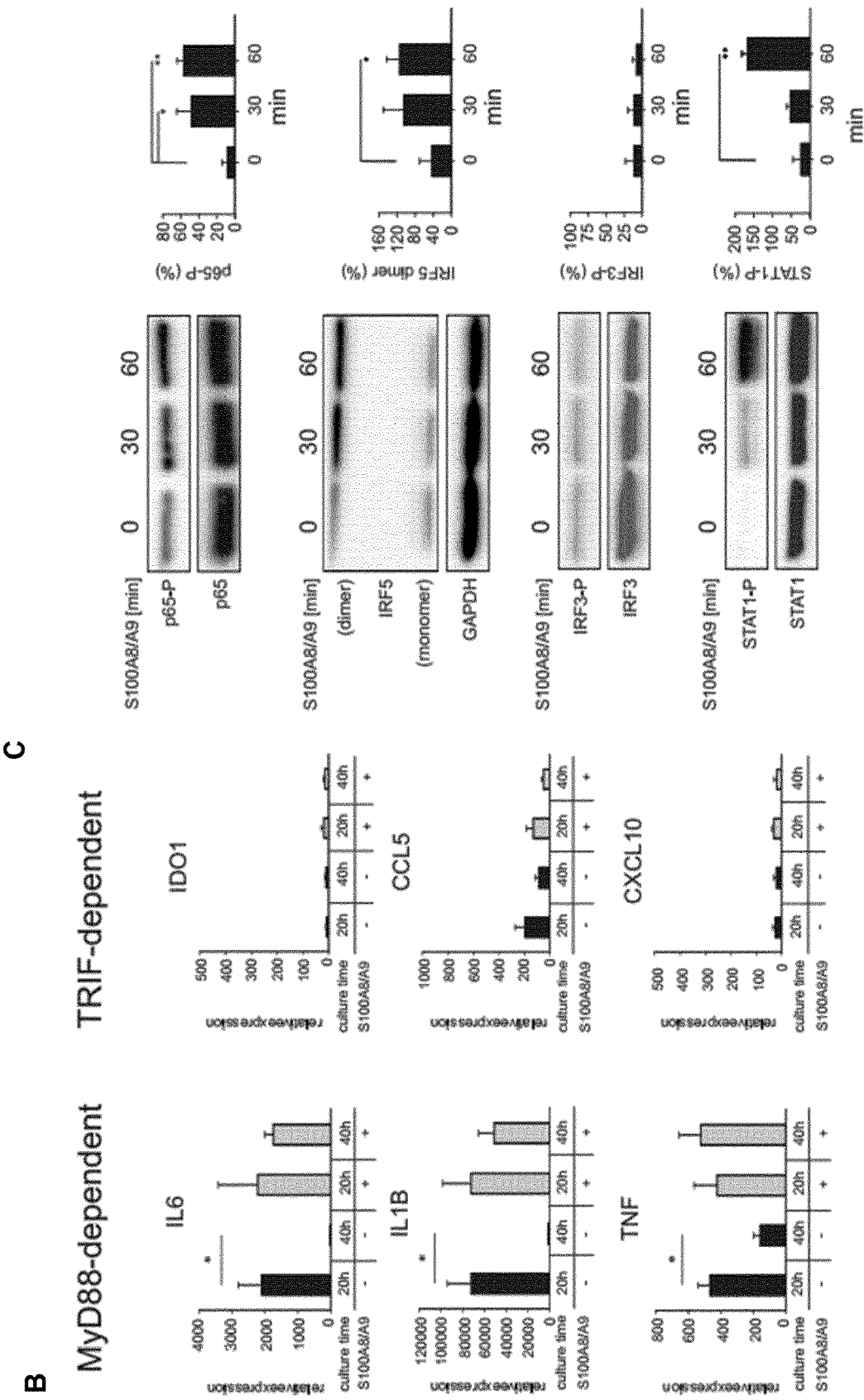
Figure 3:
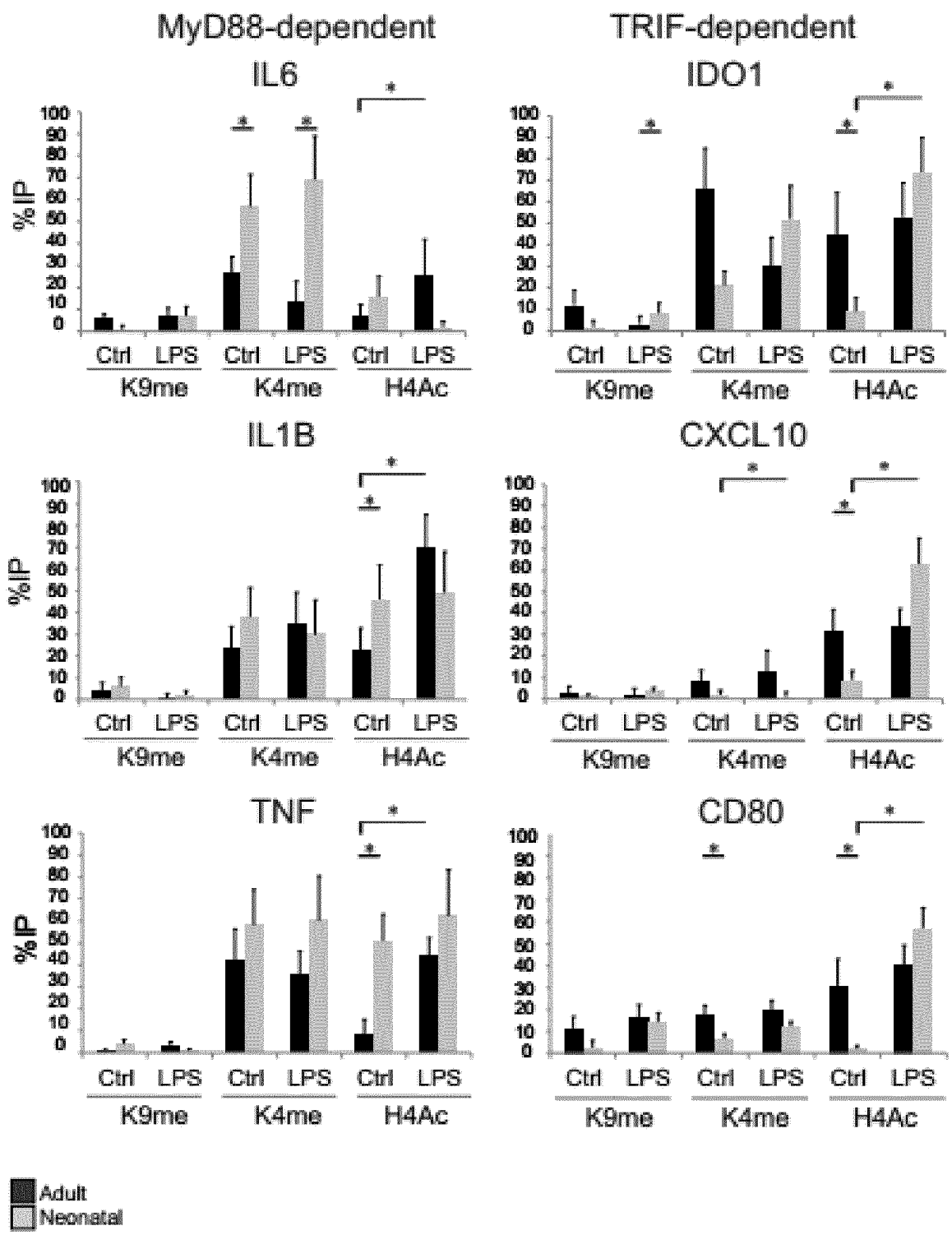
Figure 3:
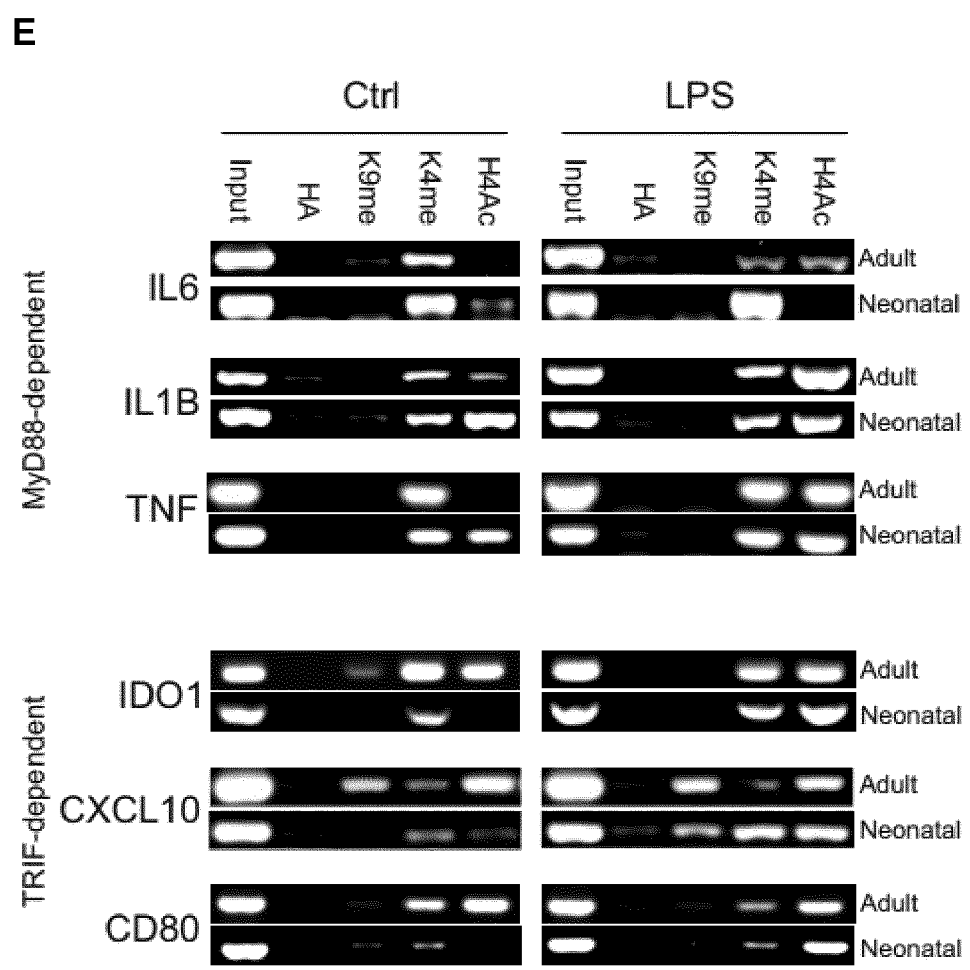

Further, the activation of transcriptional activators downstream of TLR4 (FIG. 3A) was traced. In AB-Mo, NF-κB p65 was rapidly phosphorylated after LPS treatment, which was not observed in CB-Mo. In contrast, significant nuclear accumulation of NF-κB RelB, which is linked to LPS tolerance, was observed in CB-Mo but not in AB-Mo. IRF5 presented with high stimulation-independent a priori expression and dimerization in CB-Mo, while IRF5 expression in AB-Mo only increased after LPS activation without dimerization (FIG. 3A). Together, these data documented altered activation of NF-κB that is refractory to LPS stimulation with high basal IRF5 activity in CB-Mo. Unexpectedly, IRF3 and STAT1 were similarly expressed and phosphorylated in AB-Mo and CB-Mo (FIG. 3A). Thus, no significant differences between IRF3 and STAT1 that could explain the low basal expression of TRIF-dependent genes in CB-Mo were identified.

It was previously reported that CB-Mo but not AB-Mo strongly express and release the alarmins S100A8 and S100A9, endogenous TLR4 ligands, that induce a state of hyporesponsiveness in adult monocytes very similar to ET. As shown herein, high expression of MyD88-dependent genes in CB-Mo indeed required the presence of S100A8/S100A9 during cell culture. Yet, S100A8/S100A9 had no significant influence on the low expression of TRIF-dependent genes (FIG. 3B). Moreover, S100A8/S100A9 strongly activated NF-κB and IRF5 in S100A8/S100A9-naive AB-Mo but not IRF3 (FIG. 3C). Although the alarmins activated STAT1, the rapid kinetics pointed to an IRF3-independent activation pathway. These data suggest that alarmins cause neonatal programming of MyD88/NF-κB/IRF5-dependent but not TRIF/IRF3/STAT1-dependent genes.

Differential cell programming can be explained by distinct epigenetic regulation (Saeed S. et al., Science (2014) 345: 1251086; Alvarez-Errico D. et al., Nat Rev Immunol (2015) 15: 7). Therefore the promoter-associated histone modifications by focusing on H3K9 trimethylation (H3K9me3) have been examined, which is linked to gene repression, and H3K4 trimethylation (H3K4me3) and H4K91 acetylation (H4K91ac), both of which are linked to gene activation (FIG. 3B and FIG. 3C). In AB-Mo, the MyD88-dependent genes IL-6, IL-1β, and TNFα were not significantly acetylated and increased H4K91ac expression upon LPS stimulation. In CB-Mo, however, the promoters of these genes had high baseline levels of H3K4me3 and H4K91ac, markers for actively transcribed genes. No further histone acetylation or even deacetylation was observed upon LPS challenge reminiscent of a tolerant state. These results were consistent with the alarmin-mediated pre-activation and LPS-hyporesponsiveness of IL-6, IL-1β and TNFα in CB-Mo compared to their strong inducibility in AB-Mo. In contrast, the promoter regions of IDO1, CXCL10 and CD80 had significant H3K4me3 and H4K91ac marks in AB-Mo. These did not change upon LPS stimulation, which explains the solid basal expression tonus and moderate LPS inducibility. In CB-Mo, however, the promoters of all these TRIF-dependent genes were not acetylated and barely trimethylated at baseline but rather strongly acetylated upon LPS stimulation, which is in line with a lack of basal gene expression at birth but strong inducibility by LPS. These data further illustrate that CB-Mo are not impaired in functionality but rather differentially regulated, both transcriptionally and epigenetically.

Figure 4:
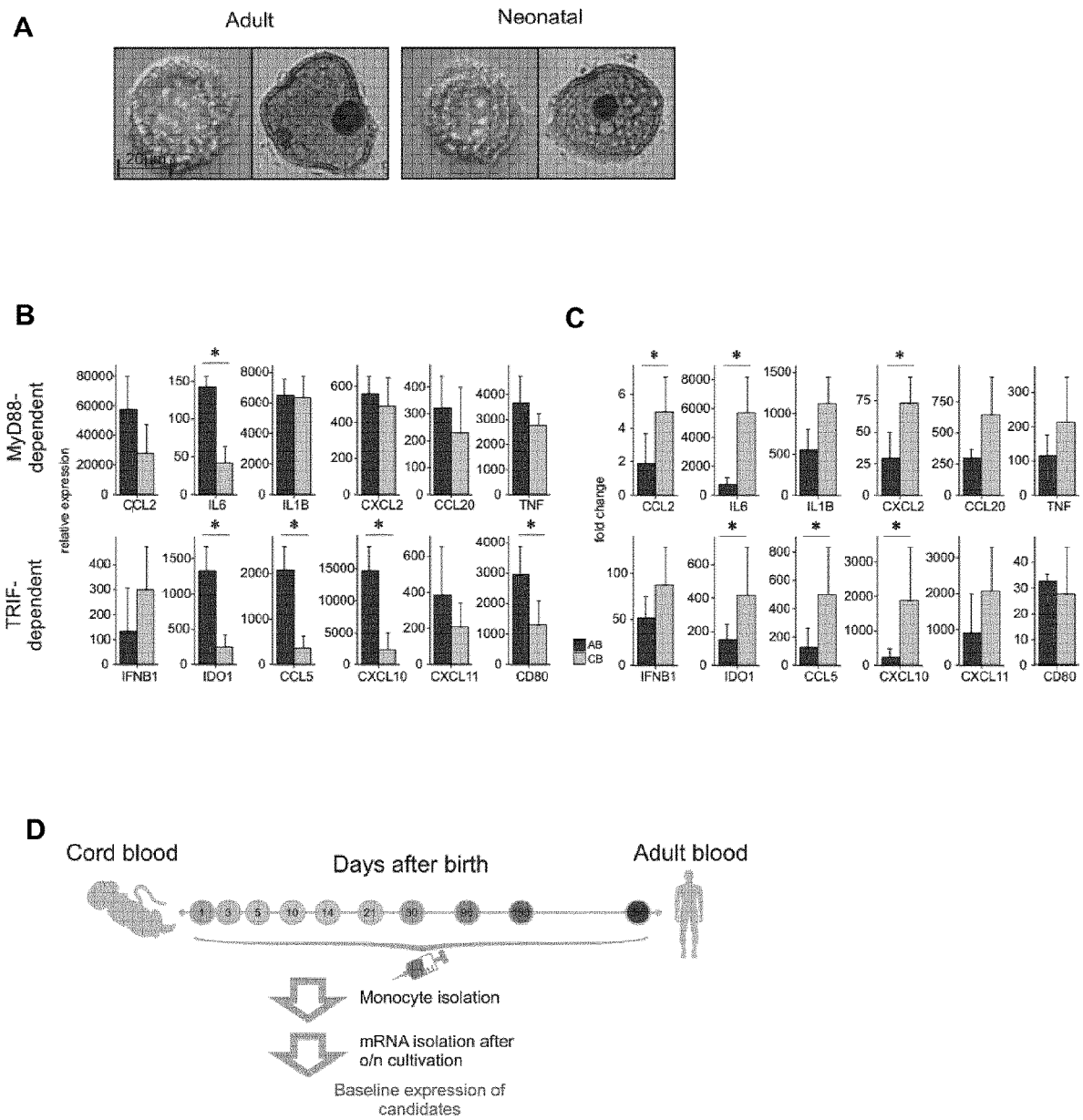
FIG. 4: Postnatal expression changes in human monocytes. (A) Morphology of macrophages derived from AB-Mo (AB-MDM) and CB-Mo (CB-MDM). Left, phase contrast; right, MGG-staining. (B), (C) Relative gene expression in untreated AB-MDM and CB-MDM (B) and LPS-induced FCs (C). Bars represent mean±s.d. (n=3) *P<0.05, Student's t-test. (D) Workflow for blood samples obtained from healthy infants (n=127) and adults (n=20). (E) Age-dependent expression of MyD88- and TRIF-dependent genes. Bars represent means±s.e.m. Significant differences were determined by ANOVA, as indicated by capped-end lines across all age groups (*P<0.05; P<0.001; *P<0.0001) and a post-hoc ANOVA t-test (open lines between age subgroups and adults, P<0.05).
Figure 4:
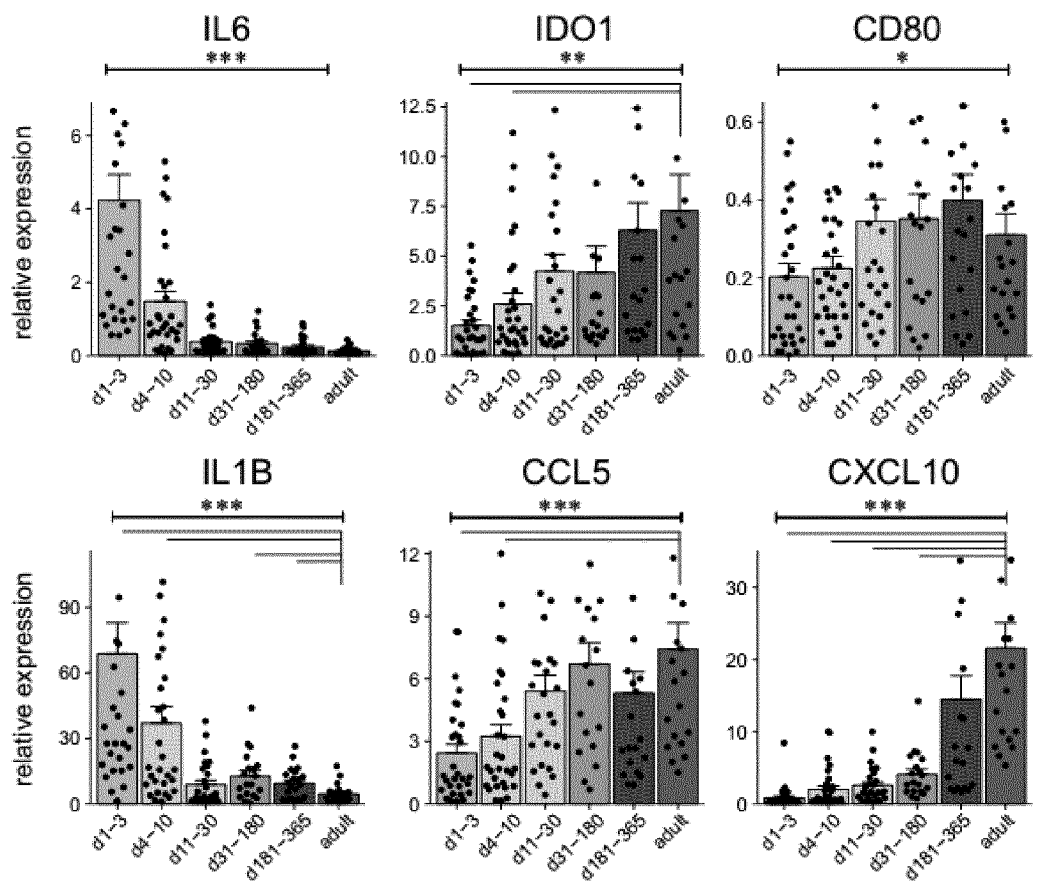

The difference between AB-Mo and CB-Mo suggested cellular reprogramming in Mo as a consequence of postnatal maturation. We attempted to mimic such reprogramming in vitro by exposing CB-Mo to AB plasma for 14 days. Cell viability and acquisition of a macrophage-like morphology (FIG. 4A) was comparable in AB-Mo and CB-Mo. After this culture period, expression of MyD88/NF-κB/IRF5-dependent genes decreased in cultured CB-Mo to a comparable or even lower level than in cultured AB-Mo (FIG. 4B) resulting in a significantly stronger inducibility by LPS (FIG. 4C). In contrast, the expression of most of the TRIF/IRF3/STAT1-dependent genes in CB-Mo did not increase during 14 days of culture (FIG. 4B) and responded to LPS stimulation with stronger expression increases (FIG. 4C). This data clearly showed that loss of alarmin-tolerization without maturation of regulatory gene programs results in an inflammatory phenotype of neonatal Mo. This is supported by our findings in S100A9−/− neonates that are prone to hyperinflammatory courses of sepsis.

Thus it could be hypothesized that TRIF/IRF3/STAT1-dependent genes need in vivo conditions and/or longer time periods for reaching adult baseline levels. Therefore, a study was performed assessing gene expression changes in vivo during the first year of life in healthy infants compared to adult volunteers (FIG. 4D). Similar as in the in vitro model, the high expression of pro-inflammatory IL-6 and IL-1β after birth rapidly decreased during the first days of life. However, TRIF-dependent genes reached expression levels comparable with those seen in healthy adults starting between 11 and 30 days for CD80 and in the second half of the first year of life for CCL5 and IDO1. CXCL10 did not even reach adult levels within the first year.

Based on these findings, a model could be proposed that explains the previously suggested impaired LPS response of the newborn immune system by a transient birth-related alarmin-induced state of unresponsiveness, particularly for MyD88-dependent genes. TRIF-dependent genes regulate emerging MyD88-dependent pro-inflammatory responses in adult Mo. As demonstrate herein, they are not yet expressed at birth but require reprogramming towards the adult phenotype over a prolonged period of time during the first year of life. Thus it can be suggested that alarmin-mediated tolerization is an essential mechanism in neonates to prevent hyperinflammatory responses to LPS, as long as the expression tonus of regulatory TRIF-dependent genes is still low after birth. However, insufficient alarmin-induced pre-activation of MyD88-dependent pro-inflammatory genes and impaired or delayed reprogramming of TRIF-dependent regulatory genes renders neonates susceptible to hyperinflammatory immune responses, thereby increasing the sepsis risk in this age group. These findings are further supported by recent observations in a murine model of neonatal sepsis, where treatment with the TRIF-dependent representative CXCL10 was protective (Cuenca A. G. et al., Infect Immun (2011) 79: 2746; Cuenca A. G. et al., J Immunol (2015) 194: 1169). During fetal development, the silencing of TRIF-dependent genes might be important to prevent the activation of adaptive immunity (Kanagavelu S. et al., Infect Immun (2015) 83: 4404; Kolb J. P. et al., Sci Signal (2014) 7: ra108), which would contribute to fetomaternal tolerance. Promoting postnatal immune maturation by using specific TLR4 agonists activating TRIF signalling could represent a valuable preventive option for newborn infants at high risk for sepsis.

Figure 8:
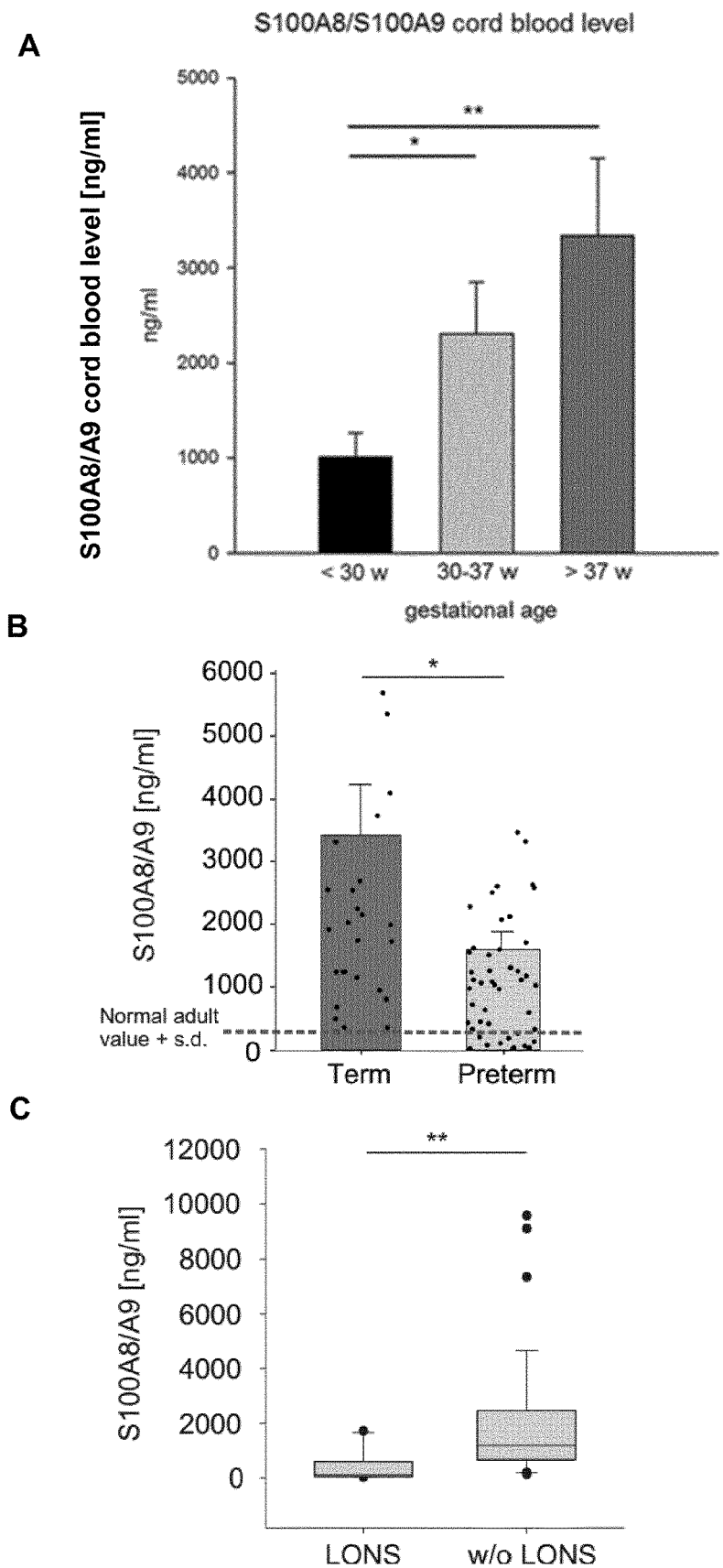
FIG. 8: S100A8/S100A9 cord blood level in dependence on gestational age. (A) Concentration of S100A8/S100A9 heterodimer in the cord blood significantly increases with gestational age of a human newborn subject. (B) S100A8/A9 levels in cord blood of term (n=31) and preterm (n=49) human newborns. Bars represent means±s.e.m., ** P<0.05 (Mann-Whitney U test). (C) S100A8/A9 cord blood levels differentiated in preterm newborns with later occurrence (n=13) or absence (n=49) of LONS. Box plots show medians and interquartile ranges±s.d., * P<0.05 (Mann-Whitney U test). (D) Birth characteristics of the group of preterm and term infants analyzed in (B) and (C) for S100A8/S100A9 level in cord blood.
Figure 9:
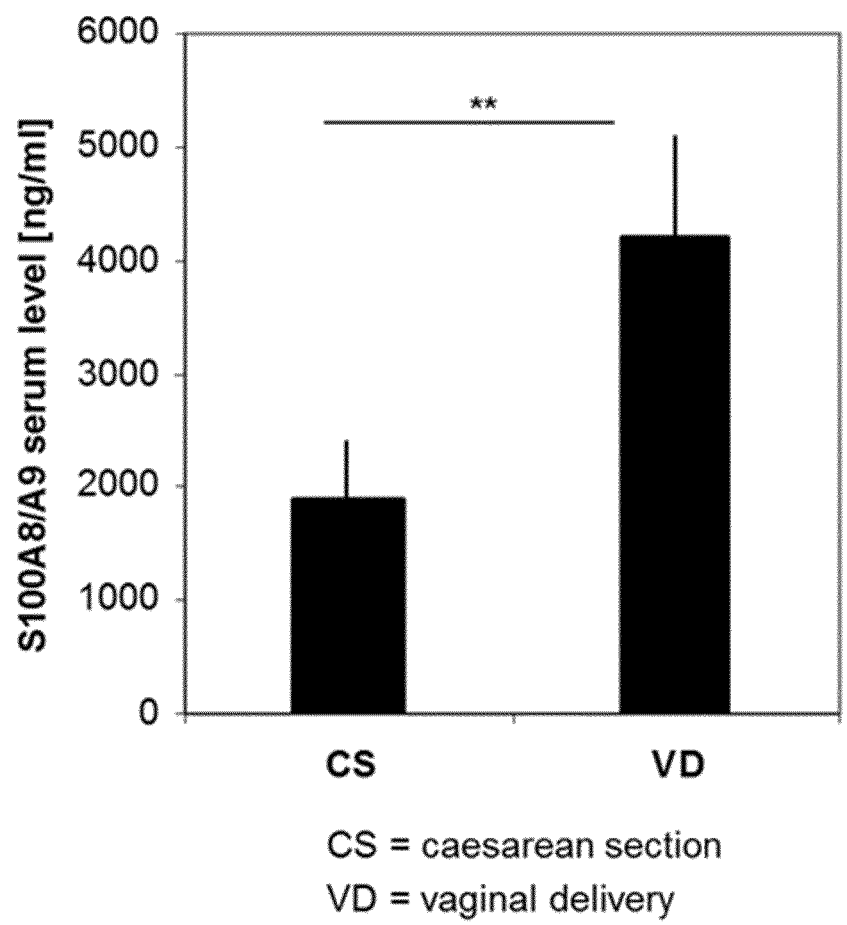
FIG. 9: S100A8/S100A9 serum level in Caesarean section and vaginally delivered human newborn subjects. Concentration of S100A8/S100A9 heterodimer in vaginal delivered human newborn subjects is significantly higher than in human newborn subjects born via Caesarean section.

In line with the above observation, it could be further demonstrated in the present invention in premature (pre-term) newborn subjects that the level of S100A8/S100A9 in the blood cord is significantly lower than the S100A8/S100A9 level in the blood cord of newborn subjects with a normal gestational age (FIG. 8). Further, it was found that the S100A8/S100A9 serum level in newborn subjects delivered by Caesarean section is significantly lower than in subjects born via vaginal delivery (FIG. 9). Instead, a massively high concentration of S100A8/S100A9 derivatives could be detected in breast milk (FIG. 10). Thus, these observations underline a possible overriding principle to prevent extreme inflammatory reactions on postnatal bacterial settlements of newborn subjects, in particular premature subjects and Caesarean section newborn which are characterized by a decreased bacterial colonization. Accordingly, the present invention describes in this connection the possibility of a preventive use of endogenous alarmins such as S100A8/S100A9 derivatives against the formation of postnatal inflammatory disorders in consequence of the newborn response towards Pathogen Associated Molecular Patterns (PAMPs), particularly LPS, such as sepsis, necrotizing enterocolitis, and bronchopulmonary dysplasia, or postnatal alteration which in consequence of the newborn response towards PAMPs directly increase the risk of the formation of a postnatal inflammatory disorder, such as disturbed microbiome development.

Figure 5:
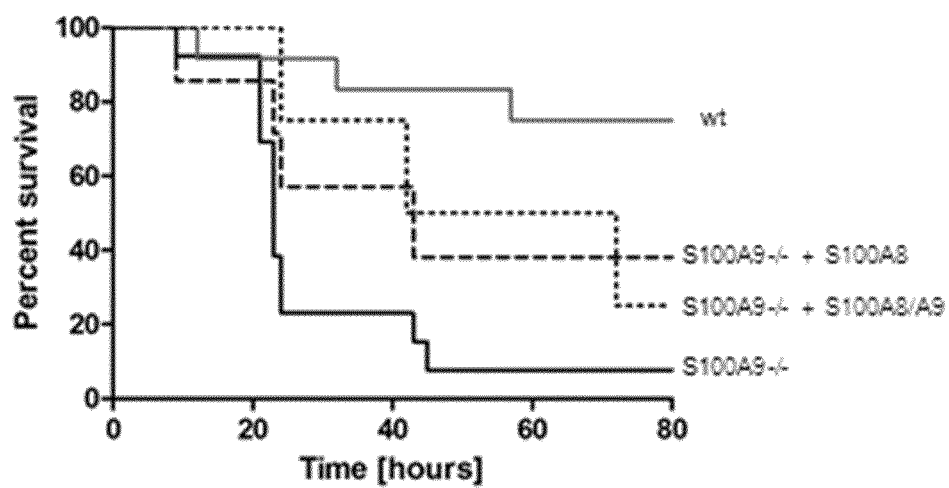
FIG. 5: Mouse endotoxin model (LPS treatment). Survival rate of S100-knock-out mice after substitution with S100A8/A9 heterodimer or S100A8 homodimer. Pre-treatment with S100A8/A9 heterodimer or S100A8 homodimer significantly protects mice against LPS-induced septic shock.
Figure 6:
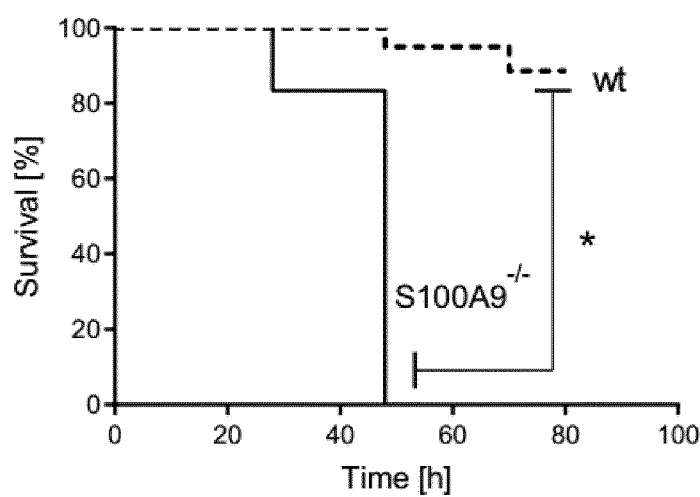
FIG. 6: Mouse staphylococcus/sepsis model. (A) Percentage of surviving wt (n=12) and S100A9$^{-/-}$ (n=16) neonates after sepsis induction by S. aureus. *P<0.0001 (Mantel-Cox test). (B) Survival rate of S100-knock-out mice after substitution with S100A8/A9 heterodimer or S100A8 homodimer. Pre-treatment with S100A8/A9 heterodimer or S100A8 homodimer significantly protects mice against LPS-induced septic shock and correlate inversely with the sepsis risk of human neonates.
Figure 6:
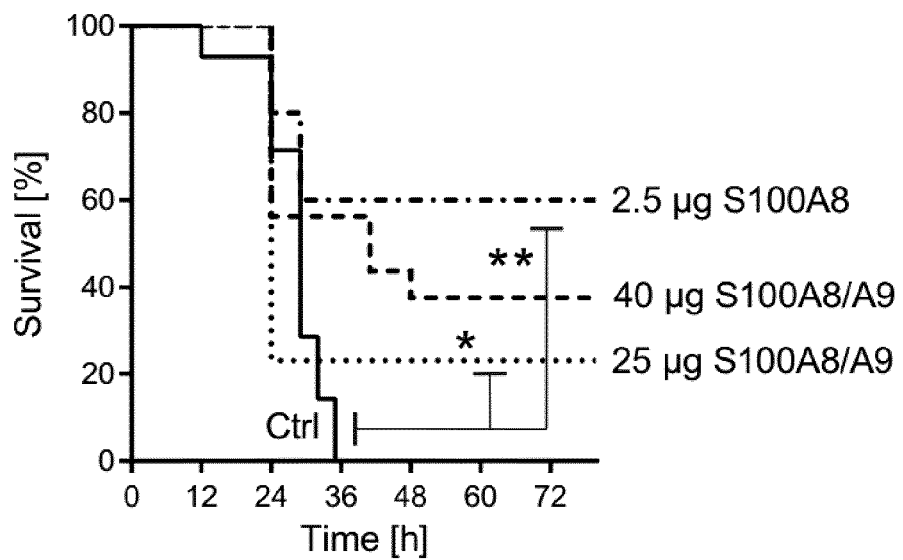
Figure 7:
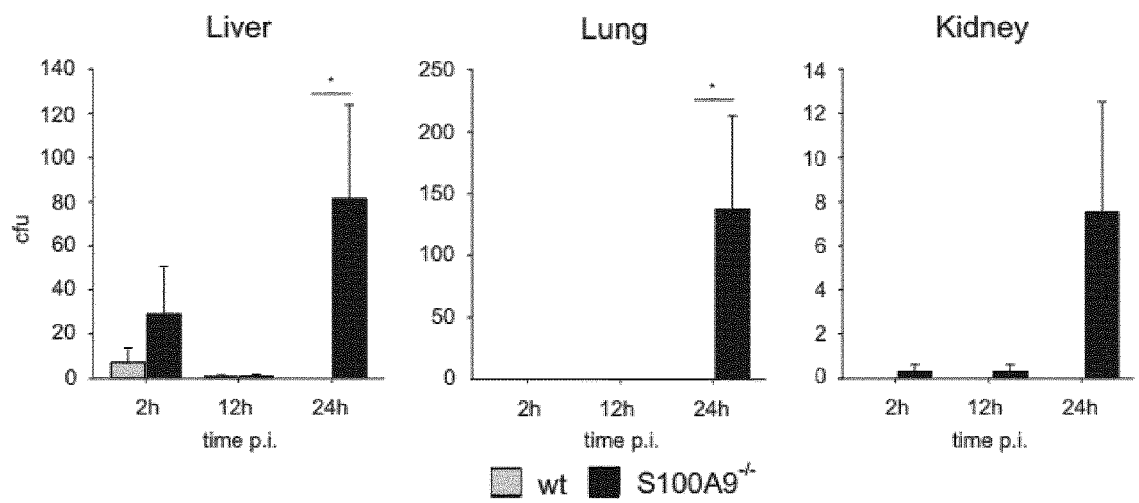
FIG. 7: Bacterial load in different mouse tissues measured as colony forming units (CFUs) per tissue. (A) Bacterial loads post infection (p.i.) (each group n=10 wt, 11 S100A9$^{-/-}$). Results are plotted as means±s.d. *P<0.05, P<0.005, *P<0.0005 (unpaired t-test). (B) CFUs in liver, lung and kidney tissue of mice with and without substitution with S100A8 homodimer. Pre-treatment with S100A8 homodimer significantly protects mice organs against bacterial load. Bacterial loads (PBS n=5. S100A8 n=11). Bars represent means±s.d. * P<0.05, ** P<0.01 (unpaired t-test).
Figure 7:
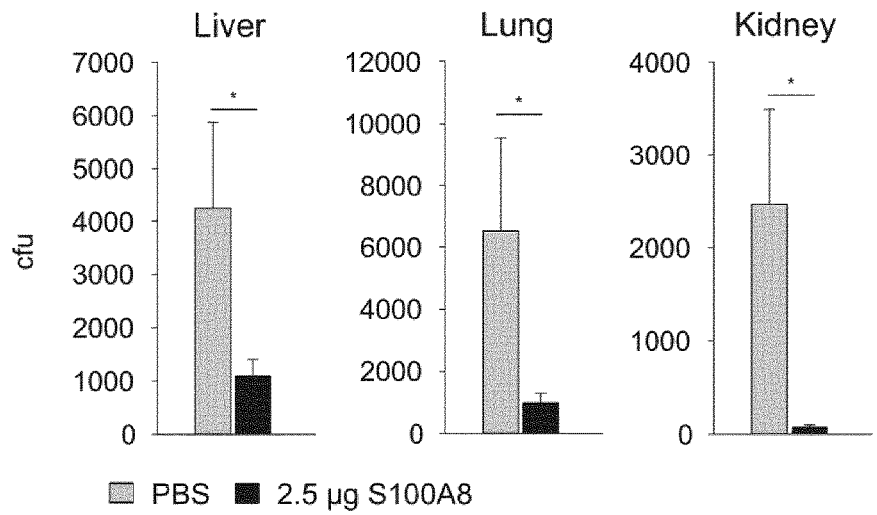

Additionally, it could be demonstrated in in vivo experiments with S100-knock-out mice that substitution with S100A8/S100A9 heterodimer or S100A8 homodimer leads in both an endotoxin (LPS administration) model as well as a staphylococcus/sepsis model to a significantly elevated survival rate of said animals (FIG. 5 and FIG. 6), which further supports the hypothesis of an alarmin-induced state of hyporesponsiveness to LPS in newborn subjects at birth. In this respect also the bacterial load of liver, lung and kidney was significantly reduced in said animals when pre-treated with S100A8/S100A9 derivatives prior to the test series (FIG. 7). Surprisingly, the highest efficacy could be observed for the S100A8 monomer, which seems to be even more efficient than the S100A8/S100A9 heterodimer. Accordingly, the preventive and therapeutic use of lower concentrations of S100A8 homodimer seems to be highly recommendable for achieving the desired effect of stress tolerance in newborn subjects.

Study Population

After written informed consent was obtained from parents, 1 ml EDTA samples were collected from healthy infants beginning on the day of birth (day 0) during the first year of life (n=127, which had routine peripheral blood drawings for the national screening program for inborn errors of metabolism or for testing bilirubin blood levels due to physiologic jaundice or for routine blood tests done prior to elective procedures or operations without underlying inflammatory diseases. Participants were prospectively enrolled between June 2011 and December 2015 at the Hannover Medical School (Hanover, Germany). Gestational age was calculated based on the last menstrual period. When early ultrasound at $11\text{-}13^{+6}$ week's gestation using the fetal Crown-Rump-Length (CRL) deviated more than seven days, dating was performed using ultrasound. Pregnancies that involved in vitro fertilization, multiple gestations, births that resulted from maternal trauma, and newborns with major anomalies, small or large-for gestational age weight and clinical or laboratory signs of amnion infection syndrome were excluded. Adult blood samples (n=20) were obtained from healthy volunteer donors with no signs of infection during the last 4 weeks.

Ethics Statement

The studies were approved by the Institutional Review Board of the Hannover Medical School (no. 6031-2011, no. 6031-2015, Research Obstetrics Biobank no. 1303-2012). Written informed consent was obtained from all participating individuals respective the parents.

Cells and Cell Culture Conditions

For all studies comparing adult and neonatal Mo, written informed consent was obtained from parents to collect 50 ml heparinized CB samples from healthy term newborns delivered vaginally. Human AB-Mo came from buffy coats of healthy donors. After Ficoll-Paque density gradient centrifugation, Mo were isolated using the Monocyte Isolation Kit II (Miltenyi Biotec, Bergisch Gladbach, Germany). For expression analyses within the study population, we used the EasySep™ Direct Human Monocyte Isolation Kit (Stemcell Technologies, Grenoble, France) to isolate Mo from the EDTA samples within 1 h of collection. The purity of isolated Mo was >90% and quality controlled by flow cytometry using PE-labelled anti-CD14 monoclonal antibody (mAb), using a FACS Canto II flow cytometer with the DIVA software V6.1.3 (all BD Biosciences, Heidelberg, Germany). After overnight (o/n) culture of $1\times10^6$ cells/ml in Teflon bags in McCoy's modified medium (Biochrom AG, Berlin, Germany) supplemented with 1% glutamine, 1% penicillin-streptomycin and 15% FBS Mo were incubated for indicated time periods with 10 ng/ml LPS or 2 µg/ml S100A8/S100A9 for gene expression studies, 100 ng/ml LPS or 10 µg/ml S100A8/S100A9 for immunoblotting analyses and 1 µg/ml LPS for ChIP assays.

Monocyte-derived macrophage-like cells (MDM) were obtained by culturing purified Mo for 14 days in RPMI 1640 supplemented with 1% glutamine, 1% penicillin-streptomycin and 10% human AB plasma. Thereby, every third day 30% of the medium was replaced by fresh macrophage medium. Air-dried and 2% PFA fixed MDM cultured in Lap-Tek chambers (Thermo Fisher Scientific, Darmstadt, Germany) were used for May-Grunwald-Giemsa (MGG, Pappenheim) staining.

Reagents

LPS (*Escherichia coli* 055:B5) was purchased from Sigma (Steinheim, Germany). Human S100A8/S100A9 complex was isolated from granulocytes, as described by Austermann et al., Cell Reports (2014) 9: 1-12.

Gene Array Expression Studies and Bioinformatic Analysis of Microarray Data

For each experimental condition (LPS, control (Ctrl)), total RNA was isolated from three individual donors using the NucleoSpin RNA II kit (Macherey-Nagel, Duren, Germany). Samples were processed for microarray hybridization using Affymetrix GeneChip® Human Genome U133A 2.0 (hgu133a) for AB-Mo and hgu133plus2 for CB-Mo as described earlier (Viemann D. et al., J Immunol (2011) 186: 164). Data were imported into the Partek Genomics Suite 6.6 (PGS; V6.14.0724) using RMA (Robust Multi-array Average, an algorithm used for background correction, $\log_2$-transformation and quantile normalization of Affymetrix expression data) prior to batch-correction. Expression values from different chip types (AB-Mo from hgu133a, CB-Mo from hgu133plus2) were combined, keeping only probes with information from both chip types resulting in 22,277 probes. Further, only one probe per gene symbol was left by selecting the probes with the highest variance among all samples resulting in 13,515 unique transcripts. Differentially expressed (DE) genes were defined by a fold-change (FC)>2 or <−2, and a false discovery rate (FDR)-corrected p<0.05.

To visualize the structure within the data, we performed Principle Component Analysis (PCA) on all present and hierarchical clustering (HC) on the 1,000 genes with the highest variance within the dataset, with default settings in PGS, based on P values according to the expression values of the samples across the conditions. For pathway enrichment analyses we imported lists of DE genes into the Reactome database of biological pathways and processes (www.reactome.org) (Fabregat A. et al., Nucleic Acids Res (2016) 44: D481-D487). Overrepresentation of pathways within groups of DE genes was computed applying a one-tailed Fisher's exact test. Only top-level pathways with a probability of p<0.0001 for overrepresentation were considered. Selected enriched Reactome pathways were visualized by a bar plot using the R package ggplot2. Enrichment P values were plot in $\log_{10}$ scale. To link DE genes to known biological functions, we used the 376 most differentially up-regulated and 319 most down-regulated genes in LPS activated CB-Mo compared to control CB-Mo, the 482 most differentially up-regulated and 780 most down-regulated genes in LPS activated AB-Mo compared to control AB-Mo and the 162 most differentially up-regulated and 517 most down-regulated genes in control AB-Mo compared to control CB-Mo (FC>4 or <−4 and FDR-corrected P value<0.05) in order to generate and visualize a network based on GO-enrichment analysis (GOEA) by using BiNGO (Maere S. et al., Bioinformatics (2005) 21: 3448), EnrichmentMap (Merico D. et al., PLoS One (2010) 5: e13984) and Word-Cloud (Oesper L. et al., Source Code Biol Med (2011) 6: 7) in Cytoscape (www.cytoscape.org). Color and size of nodes represent corresponding FDR-adjusted enrichment P values (Q values). Overlaps of genes between GO-terms were indicated by edges. To determine age-dependent changes due to activation using gene regulatory networks, we built the union of DE genes comparing LPS activated AB-Mo with control AB-Mo and DE genes, comparing LPS activated CB-Mo with control CB-Mo. The expression values of these genes were used for co-expression analysis (CEA) over all 12 data sets using BioLayout3D (Theocharidis A. et al., Nat Protoc (2009) 4: 1535). Applying a correlation cutoff of 0.7 resulted in a co-expression network with 442 nodes (genes). The calculated gene-gene pairs together with their Pearson correlation coefficient were exported from BioLayout3D and imported into Cytoscape using force-directed layout for visualization. Cytoscape was used to map further information onto the network. E.g. we mapped FC values (based on an ANOVA model) or group FC values (based on the comparison of each condition with the mean over all conditions) for each condition individually onto the network. To identify small differences between CB-Mo and AB-Mo based on co-expression network analysis, we marked genes with FCs>1.2 or <−1.2 comparing control CB-Mo with control AB-Mo which resulted in two gene clusters. The genes of each gene cluster were then used for TF binding site (TFBS) prediction using iRegulon (Janky R. et al., PLoS Comput Biol (2014) 10: e1003731). For the overrepresentation of transcription factor analysis, the R package pcaGoPromoter V1.12.0 (Hansen M. et al., PLoS One (2012) 7: e32394) was used. PCA loadings were extracted to obtain the probe identifiers from the top 2.5% of genes contributing to the first (PC1) and second principal component (PC2) in positive and negative direction. These top contributing genes were further considered for prediction of regulatorytranscription factor networks. Overrepresentation analysis of predicted transcription factor binding sites was performed using the primo algorithm with the following parameters: P value cutoff for significance=0.05, adjusting P values for multiple testing with FDR, and percentage of promoters that should be bound by a transcription factor>=90%. Microarray data are MIAME compliant and deposited in GEO (GSE78697).

Quantitative Real Time PCR (qRT-PCR)

RNA was isolated using the NucleoSpin RNA II kit. Quality was assessed using an Agilent 2100 BioAnalyzer with the RNA 6000 Nano Kit (RNA Integrity Number (RIN)>7.0) (Agilent, Santa Clara, Calif.). qRT-PCR was performed as described in Viemann D. et al., J Leukoc Biol (2006) 80: 174.

The primers used were GAPDH (F: GCAAATTC-CATGGCACCGT (SEQ ID NO: 1), R: GCCCCACTTGAT-TTTGGAGG (SEQ ID NO: 2)), CCL2 (F: TCGCCTCCAG- CATGAAAGTC (SEQ ID NO: 3), R: TTGCATCTGGCTGAGCGAG (SEQ ID NO: 4)), IL-6 (F: AGAGGCACTGGCAGAAAACAAC (SEQ ID NO: 5), R: AGGCAAGTCTCCTCATTGAATCC (SEQ ID NO: 6)), IL-1β (F: GCGGCCAGGATATAACTGACTTC (SEQ ID NO: 7), R: TCCACATTCAGCACAGGACTCTC (SEQ ID NO: 8)), CXCL2 (F: ACATCCAAAGTGTGAAGGT-GAAGTC (SEQ ID NO: 9), R: AAGCTTTCTGCCCAT-TCTTGAGT (SEQ ID NO: 10)), CCL20 (F: ACCCTCCAT-GATGTGCAAGTG (SEQ ID NO: 11), R: TTCTGGAATGGAATTGGACATAGC (SEQ ID NO: 12)), TNFα (F: CTTCTCGAACCCCGAGTGAC (SEQ ID NO: 13), R: TGAGGTACAGGCCCTCTGATG (SEQ ID NO: 14)), IFNB1 (F: TCTGGCACAACAGGTAGTAGGC (SEQ ID NO: 15), R: GAGAAGCACAACAGGAGAGCAA (SEQ ID NO: 16)), 001 (F: TGCAGGC-CAAAGCAGCGTCT (SEQ ID NO: 17), R: GAGCAG-CATGTCCTCCACCAGC (SEQ ID NO: 18)), CCL5 (F: CAGTGGCAAGTGCTCCAACC (SEQ ID NO: 19), R: CCATCCTAGCTCATCTCCAAAGAGT (SEQ ID NO: 20)), CXCL10 (F: AAGGATGGACCACACAGAGG (SEQ ID NO: 21), R: TGGAAGATGGGAAAGGTGAG (SEQ ID NO: 22)), CXCL11 (F: CAGAATTCCACTGCCCAAAGG (SEQ ID NO: 23), R: GTAAACTCC-GATGGTAACCAGCC (SEQ ID NO: 24)) and CD80 (F: CTGCTTTGCCCCAAGATGC (SEQ ID NO: 25), R: CAGATCTTTTCAGCCCCTTGC (SEQ ID NO: 26)). Sample data are presented as fold induction of gene expression compared to control cells using the comparative Ct method or as relative expression to the housekeeping control gene GAPDH.

Immunoblotting

To detect phosphorylated relative to total p65, IRF3 and STAT1 and for the detection of IRF5 relative to glyceraldehyde 3-phosphate dehydrogenase (GAPDH) whole cell lysates were obtained by lysis of $5 \times 10^6$ cells in RIPA buffer containing protease and phosphatase inhibitors as described in Viemann D. et al., Blood (2005) 105: 2955. For the detection of nuclear RelB accumulation relative to histone deacetylase 1 (HDAC1) nuclear cell extracts were prepared using the NE-PER Nuclear and Cytoplasmic Extraction kit (Thermo Fisher Scientific). SDS-PAGE and Western blot staining were performed as described earlier (Viemann D. et al., Blood (2005) 105: 2955; Viemann D. et al., Blood (2004) 103: 3365). The primary anti-human antibodies (Abs) p-NF-κB p65 (Ser 311), NF-κB p65 (C-20), RelB (C-19), IRF-5 (10T1), GAPDH (FL-335) and IRF-3 (FL-425) were from Santa Cruz Biotechnology, p-IRF3 (Ser 396) and p-STAT1 (Tyr701) from Thermo Fisher Scientific, and HDAC1 (10E2), STAT1 and the appropriate anti-mouse and anti-rabbit horseradish peroxidase conjugated secondary Abs from Cell Signaling (Leiden, Netherlands). Protein bands were visualized using the enhanced chemiluminescence system and quantified by densitometric analysis using the ChemiDoc MP System with Image Lab Software v. 4.0 (all Bio-Rad Laboratories, Munchen, Germany).

ChIP Assays

ChIP assays were carried out in control and 2-h LPS-stimulated AB-Mo and CB-Mo. Cells ($5 \times 10^6$ per condition) were harvested and fixed with 1% formaldehyde for 10 min at RT and quenched for 10 min by 125 mM glycine. After washing, the cells were lysed in 1% SDS lysis buffer for 10 min on ice, the DNA was sheared by sonification (Bandelin Sonoplus HD2070 (Berlin, Germany): 10×30 sec, 35% power, no cycle) and an aliquot kept as an input control. 100-200 μl of chromatin lysate (corresponding to $1 \times 10^6$ cells), respectively, were 1:10 diluted with ChIP-dilution buffer (0.01% SDS, 1.1% Triton x-100, 1.2 mM EDTA, 16.7 mM Tris pH:8,1, 167 mM NaCl), precleared for 90 min with NG-Agarose beads (Thermo Fisher Scientific). After overnight immunoprecipitation (IP) at 4° C. with specific polyclonal Abs against histone H3 (tri methyl K4), histone H3 (tri methyl K9) and histone H4 (acetyl K91) and a polyclonal control anti-HA tag Ab (all Abcam, Cambridge, USA), DNA-protein-complexes were extracted with protein NG-Agarose beads. After stringent washing, the cross-linking between input respective IP DNA and protein was reversed, and proteins were digested with 100 μg proteinase K (65° C. overnight). DNA was purified using the ChIP DNA Clean & Concentrator kit (Zymo Research, Irvine, USA) and analyzed by PCR using the PCR Mastermix from Genaxxon (Ulm, Germany). Primers were used for the promoters of 1L6 (F: CCCCCTAGTTGTGTCTTGCC (SEQ ID NO: 27), R: CTTTGTTGGAGGGTGAGGGT (SEQ ID NO: 28)), IL-1β (F: GGCATTGATCTGGTTCATCCA (SEQ ID NO: 29), R: GGCAGAGAACATACGGTATGCA (SEQ ID NO: 30)), CCL20 (F: AGCAGGAAGTTTTCCTTGCG (SEQ ID NO: 31), R: AGAAGGCGTGTTGCCACAT (SEQ ID NO: 32)), TNFα (F: CCTCCAGGGTCCTACACACA (SEQ ID NO: 33), R: TTGGGGACACACAAGCATCA (SEQ ID NO: 34)), 001 (F: AGCGCGAGAGCTATTCTAGACTGT (SEQ ID NO: 35), R: AGAAAC-CAAGTTGCCCGTTCCTCT (SEQ ID NO: 36)), CCL5 (F: TGGGAGAGACCCTATGACCAGGA (SEQ ID NO: 37), R: GGCAGTTGATCTGAGCTGGGCA (SEQ ID NO: 38)), CXCL10 (F: ACCACTCTCTCTCCTTCCAACT (SEQ ID NO: 39), R: TAGGCCAAGCTCTGTTATGCTAC (SEQ ID NO: 40)), CXCL11 (F: TCCCACCAACACTCACAT-AAGG (SEQ ID NO: 41), R: TTAATGGGTAGGTGG-GAAAGACAG (SEQ ID NO: 42)) and CD80 (F: AGGCCCCTTCTGCCAATACA (SEQ ID NO: 43), R: AGTTTGTGGCAGAGCTTAGTGG (SEQ ID NO: 44)). PCR products were run on a 1.5% agarose gel, quantified with Image Lab Software v. 4.0 and normalized to the input, respectively (100%).

Mouse Endotoxin Model (LPS Treatment)

C57BL/6 mice (wild-type (wt); Harlan Laboratories) and S100A9 knock-out mice (−/−) (Manitz et al., Mol. Cell. Biol. (2008) 29: 1034-1043) were used and housed pathogen free. Septic shock was induced in 2-month-old WT mice by intraperitoneal injection of 40 mg LPS (Escherichia coli 055:B5) and 680 mg D-Gal (Sigma) per kg body weight, respectively. In parallel, mice were pretreated by intravenous injection of 100 ng LPS or 300 mg S100A8/S100A9 per mouse, followed by a LPS/D-Gal challenge 24 hr later. In additional approaches, S100A8/S100A9 complex was injected twice (12 hr and 24 hr) before LPS/D-Gal challenge. The survival of challenged mice was analyzed for 48 hr. Neonatal WT and S100A9$^{-/-}$ mice were used at the age of 2 days. Pups were subcutaneously injected with 10 mg LPS or PBS (control). For cytokine expression analysis, blood and organs were harvested 2 hr after LPS treatment. For survival studies, mice were observed for 80 hr.

Cytokine Assays and ELISA

Cytokine levels in mouse plasma were studied by using the murine FlowCytomix Sets obtained from eBioscience (Vienna, Austria). For cytokine studies in supernatants of Mo cultures we used the human FlexSets for IL-6, IL-1β, IL-10 and TNF-α from BD Biosciences. Serum concentrations of human S100A8/A9 were determined by an ELISA as described in Austermann et al., Cell Reports (2014) 9: 1-12, Vogl, T. et al., Nat. Med. (2007) 13: 1042-1049 in WO 2016/116881.

Mice and Model of *S. aureus* Induced Neonatal Sepsis

C57BL/6 mice (wild-type (wt); Harlan Laboratories) and S100A9 knock-out mice (−/−) were used and housed under specific pathogen-free conditions. Neonatal wt and S100A9$^{-/-}$ mice were used at the age of 2 days to induce sepsis by subcutaneous (s.c.) injection of 20 µl of bacterial suspensions containing 7×10$^4$ CFU *S. aureus* strain Newman (GenBank accession number AP009351.1). Control neonates received 20 µl PBS s.c. For pre-treatment studies, S100A9$^{-/-}$ pups were injected at the age of 1 day with 25 µg or 40 µg S100A8/A9 or 2.5 µg S100A8 in 20 µl of PBS intraperitoneally (i.p.). Mice pre-treated with PBS alone served as controls. Sepsis was induced 40 h after pre-treatment by injecting 7×10$^4$ CFU *S. aureus* s.c. Mice were monitored for survival over a time period of 80 h. For gene expression, cytokine studies and bacterial load analyses mice were sacrificed by decapitation 24 h after bacterial inoculation to harvest plasma and organs. For RNA isolation, right liver lobes were snap-frozen in liquid nitrogen and finely ground prior to resuspension in RNA lysis buffer and storage at −80° C. For the determination of bacterial loads, right lungs, right liver lobes and both kidneys were harvested and homogenized using a 70 µm cell strainer. Organ homogenates were plated in serial dilutions on blood agar plates. *S. aureus* colonies were counted after 18 h of incubation at 37° C.

Ex Vivo Infection of Human Monocytes with *S. aureus*

Freshly isolated adult and neonatal human Mo were seeded at a concentration of 2×10$^6$ cells/ml in supplemented McCoy's modified medium without adding antibiotics. To mimic the neonatal situation adult Mo were additionally cultured in the presence of 10 µg/ml human S100A8/A9 or 100 ng/ml human S100A8. After overnight incubation cells were infected with *S. aureus* strain Newman at a multiplicity of infection (MOI) of 0.1 and 1.0 for 3 h and 6 h. One hour p.i. extracellular bacteria were killed by adding gentamicin at a final concentration of 100 µg/ml. Supernatants were collected and stored at −80° C. until cytokine analyses per performed. Cells were harvested and counted to determine the proportion of surviving Mo of seeded Mo. Then cells were lysed by the addition of sterile water. Serial dilutions were plated on blood agar plates. *S. aureus* colonies were counted after 18 h of incubation at 37° C. To assess phagocytosis freshly grown bacterial suspensions of *S. aureus* strain Newman in late logarithmic phase were heat-inactivated for 30 min in a 95° C. water bath before labeling for 30 min on ice with FITC solution (Sigma) at a final concentration 0.004%. FITC-labeled bacteria were stored at −20° C. until use. Human Mo isolated and cultured as described above were incubated at 37° C. and at 0° C. (negative controls) with the heat-inactivated FITC-conjugated *S. aureus* at a MOI of 20. Cells were harvested at 0 min, 30 min and 60 min, fixed in 2% PFA analyzed by flow cytometry. The phagocytosis rate was defined as the percentage of FITC-positive Mo at 30 min or 60 min—the percentage of FITC-positive Mo at 0 min.

S100A8/S100A9 Cord Blood Level in Dependence on Gestational Age

Cord blood was obtained directly after delivery and serum was frozen at −80° C. S100A8/S100A9 level was afterwards determined by a S100A8/S100A9-ELISA as described in Austermann et al., Cell Reports (2014) 9: 1-12, Vogl,T. et al., Nat. Med. (2007) 13: 1042-1049 in WO 2016/116881.

S100A8/S100A9 Serum Level in Caesarean Section and Vaginally Delivered Human Newborn Subjects Cord blood was obtained directly after delivery and serum was frozen at −80° C. S100A8/S100A9 level was afterwards determined by a S100A8/S100A9-ELISA as described in Austermann et al., Cell Reports (2014) 9: 1-12, Vogl,T. et al., Nat. Med. (2007) 13: 1042-1049 in WO 2016/116881.

S100A8/S100A9 Concentration in Human Breast Milk

Breast milk samples were centrifuged at 1300 rpm for 10 minutes to remove cells and particulates. Afterward, milk supernatants were frozen at −80° C. and S100A8/S100A9 level was determined by the S100A8/S100A9-ELISA as described in Austermann et al., Cell Reports (2014) 9: 1-12, Vogl, T. et al., Nat. Med. (2007) 13: 1042-1049 in WO 2016/116881.

Statistical Analysis

Statistical tests applied for microarray data analysis and TFBS overrepresentation analyses are described above. The statistical significance of qRT-PCR and densitometric analyses was calculated using the two-tailed Student's t-test. Age dependency of gene expression was evaluated by running a one-way ANOVA followed by a post-hoc two-tailed t-test. P values of <0.05 were judged to be significant.

The invention claimed is:

1. A method for the prevention or treatment of dysbiosis, sepsis, necrotizing enterocolitis, or bronchopulmonary dysplasia in a newborn subject, said method comprising administering a therapeutically effective amount of S100A8 or S100A9 homodimer or S100A8/A9 heterodimer to the subject in need thereof.

2. The method according to claim 1, wherein said newborn subject is a premature newborn subject or a newborn subject delivered by Caesarean section.

3. The method according to claim 1, wherein said S100A8 or S100A9 homodimer or said S100A8/A9 heterodimer induces microbial hyporesponsiveness of myeloid cells in said subject.

4. The method according to claim 1, wherein said S100A8 or S100A9 homodimer or said S100A8/A9 heterodimer induces immune and stress tolerance.

5. The method according to claim 1, wherein for preventing dysbiosis, sepsis, necrotizing enterocolitis, or bronchopulmonary dysplasia the newborn subject is administered said S100A8/S100A9 homodimer or S100A8/A9 heterodimer for at least 24 hours after birth.

6. The method according to claim 1, wherein said dysbiosis, sepsis, necrotizing enterocolitis, or bronchopulmonary dysplasia appears within the first month of life.

7. The method according to claim 1, wherein said sepsis is an early onset sepsis or a late onset sepsis.

8. The method according to claim 1, wherein said sepsis is characterized by at least one clinical symptom selected from the group consisting of apnea, bradycardia, desaturation, instability of body temperature and feeding intolerance.

9. The method according to claim 1, wherein said enterocolitis is characterized by at least one of the following symptoms:
  a) bloody mucoid stools,
  b) abdominal distension,
  c) emesis,
  d) radiographic evidence of pneumatosis intestinalis,
  e) portal venous gas,
  f) hematologic abnormalities,
  g) thrombocytopenia with a platelet count lower than 100,000/mm$^3$,
  h) neutropenia with an absolute neutrophil count lower than 2000/mm$^3$, and
  i) left shift of segmented neutrophils with a ratio of immature to total neutrophils of 0.18 or higher.

10. The method according to claim 1, wherein said bronchopulmonary dysplasia is characterized by at least one of the following symptoms:
  (a) need of oxygen therapy, and
  (b) susceptibility to infection.

11. The method according to claim 1, wherein said dysbiosis is characterized by a decreased microbial profile as compared to a newborn subject having a normal microbiome development.

12. The method according to claim 1, wherein said dysbiosis is a disturbed intestinal microbiome development, a disturbed respiratory microbiome development and/or a disturbed cutaneous microbiome development.

13. The method according to claim 1, wherein said newborn subject is a mammalian subject.

14. The method according to claim 1, wherein said S100A8 or S100A9 homodimer or said S100A8/A9 heterodimer is administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

15. A method of reducing severity of symptoms of dysbiosis, sepsis, necrotizing enterocolitis, or bronchopulmonary dysplasia in a newborn subject, said method comprising administering a therapeutically effective amount of S100A8 or S100A9 homodimer or S100A8/A9 heterodimer to the subject in need thereof.

16. The method according to claim 1, wherein said sepsis is characterized by the presence of at least three of the following characteristics within 48 hours after onset of said clinical symptom(s):
- a) C reactive protein (CRP) value higher than 20 mg/l,
- b) a hematologic abnormality,
- c) neutropenia with an absolute neutrophil count lower than 2000/mm$^3$,
- d) left shift of segmented neutrophils with a ratio of immature to total neutrophils of 0.18 or higher,
- e) radiographic evidence of pneumonia,
- f) cultural evidence of infection,
- g) green amniotic fluid,
- h) premature rupture of membranes, and
- i) signs of infection of the mother.

17. The method of claim 16 wherein the hematologic abnormality is thrombocytopenia with a platelet count lower than 100,000/mm$^3$.

* * * * *

SEQUENCE LISTING

<160> NUMBER OF SEQ ID NOS: 44

<210> SEQ ID NO 1
<211> LENGTH: 19
<212> TYPE: DNA
<213> ORGANISM: Artificial
<220> FEATURE:
<223> OTHER INFORMATION: GAPDH fwd primer

<400> SEQUENCE: 1
gcaaattcca tggcaccgt                                      19

<210> SEQ ID NO 2
<211> LENGTH: 20
<212> TYPE: DNA
<213> ORGANISM: Artificial
<220> FEATURE:
<223> OTHER INFORMATION: GAPDH rev primer

<400> SEQUENCE: 2
gccccacttg attttggagg                                              20

<210> SEQ ID NO 3
<211> LENGTH: 20
<212> TYPE: DNA
<213> ORGANISM: Artificial
<220> FEATURE:
<223> OTHER INFORMATION: CCL2 fwd primer

<400> SEQUENCE: 3
tcgcctccag catgaaagtc                                              20

<210> SEQ ID NO 4
<211> LENGTH: 19
<212> TYPE: DNA
<213> ORGANISM: Artificial
<220> FEATURE:
<223> OTHER INFORMATION: CCL2 rev primer

<400> SEQUENCE: 4
ttgcatctgg ctgagcgag                                               19

<210> SEQ ID NO 5
<211> LENGTH: 22
<212> TYPE: DNA
<213> ORGANISM: Artificial
<220> FEATURE:
<223> OTHER INFORMATION: IL-6 fwd primer

<400> SEQUENCE: 5
agaggcactg gcagaaaaca ac                                           22

<210> SEQ ID NO 6
<211> LENGTH: 23
<212> TYPE: DNA
<213> ORGANISM: Artificial
<220> FEATURE:
<223> OTHER INFORMATION: IL-6 rev primer

<400> SEQUENCE: 6
aggcaagtct cctcattgaa tcc                                          23

<210> SEQ ID NO 7
<211> LENGTH: 23
<212> TYPE: DNA
<213> ORGANISM: Artificial
<220> FEATURE:
<223> OTHER INFORMATION: IL-1beta fwd primer

<400> SEQUENCE: 7
gcggccagga tataactgac ttc                                          23

<210> SEQ ID NO 8
<211> LENGTH: 23
<212> TYPE: DNA
<213> ORGANISM: Artificial
<220> FEATURE:
<223> OTHER INFORMATION: IL-1beta rev primer

<400> SEQUENCE: 8
tccacattca gcacaggact ctc                                          23

<210> SEQ ID NO 9
<211> LENGTH: 25
<212> TYPE: DNA
<213> ORGANISM: Artificial

```
<220> FEATURE:
<223> OTHER INFORMATION: CXCL2 fwd primer

<400> SEQUENCE: 9
acatccaaag tgtgaaggtg aagtc                                          25

<210> SEQ ID NO 10
<211> LENGTH: 23
<212> TYPE: DNA
<213> ORGANISM: Artificial
<220> FEATURE:
<223> OTHER INFORMATION: CXCL2 rev primer

<400> SEQUENCE: 10
aagctttctg cccattcttg agt                                            23

<210> SEQ ID NO 11
<211> LENGTH: 21
<212> TYPE: DNA
<213> ORGANISM: Artificial
<220> FEATURE:
<223> OTHER INFORMATION: CCL20 fwd primer

<400> SEQUENCE: 11
accctccatg atgtgcaagt g                                              21

<210> SEQ ID NO 12
<211> LENGTH: 24
<212> TYPE: DNA
<213> ORGANISM: Artificial
<220> FEATURE:
<223> OTHER INFORMATION: CCL20 rev primer

<400> SEQUENCE: 12
ttctggaatg gaattggaca tagc                                           24

<210> SEQ ID NO 13
<211> LENGTH: 20
<212> TYPE: DNA
<213> ORGANISM: Artificial
<220> FEATURE:
<223> OTHER INFORMATION: TNFalpha fwd primer

<400> SEQUENCE: 13
cttctcgaac cccgagtgac                                                20

<210> SEQ ID NO 14
<211> LENGTH: 21
<212> TYPE: DNA
<213> ORGANISM: Artificial
<220> FEATURE:
<223> OTHER INFORMATION: TNFalpha rev primer

<400> SEQUENCE: 14
tgaggtacag gccctctgat g                                              21

<210> SEQ ID NO 15
<211> LENGTH: 22
<212> TYPE: DNA
<213> ORGANISM: Artificial
<220> FEATURE:
<223> OTHER INFORMATION: IFNB1 fwd primer

<400> SEQUENCE: 15
tctggcacaa caggtagtag gc                                             22
```

```
<210> SEQ ID NO 16
<211> LENGTH: 22
<212> TYPE: DNA
<213> ORGANISM: Artificial
<220> FEATURE:
<223> OTHER INFORMATION: IFNB1 rev primer

<400> SEQUENCE: 16
gagaagcaca acaggagagc aa                                              22

<210> SEQ ID NO 17
<211> LENGTH: 20
<212> TYPE: DNA
<213> ORGANISM: Artificial
<220> FEATURE:
<223> OTHER INFORMATION: IDO1 fwd primer

<400> SEQUENCE: 17
tgcaggccaa agcagcgtct                                                 20

<210> SEQ ID NO 18
<211> LENGTH: 22
<212> TYPE: DNA
<213> ORGANISM: Artificial
<220> FEATURE:
<223> OTHER INFORMATION: IDO1 rev primer

<400> SEQUENCE: 18
gagcagcatg tcctccacca gc                                              22

<210> SEQ ID NO 19
<211> LENGTH: 20
<212> TYPE: DNA
<213> ORGANISM: Artificial
<220> FEATURE:
<223> OTHER INFORMATION: CCL5 fwd primer

<400> SEQUENCE: 19
cagtggcaag tgctccaacc                                                 20

<210> SEQ ID NO 20
<211> LENGTH: 25
<212> TYPE: DNA
<213> ORGANISM: Artificial
<220> FEATURE:
<223> OTHER INFORMATION: CCL5 rev primer

<400> SEQUENCE: 20
ccatcctagc tcatctccaa agagt                                           25

<210> SEQ ID NO 21
<211> LENGTH: 20
<212> TYPE: DNA
<213> ORGANISM: Artificial
<220> FEATURE:
<223> OTHER INFORMATION: CXCL10 fwd primer

<400> SEQUENCE: 21
aaggatggac cacacagagg                                                 20

<210> SEQ ID NO 22
<211> LENGTH: 20
<212> TYPE: DNA
<213> ORGANISM: Artificial
<220> FEATURE:
<223> OTHER INFORMATION: CXCL10 rev primer
```

-continued

```
<400> SEQUENCE: 22
tggaagatgg gaaaggtgag                                        20

<210> SEQ ID NO 23
<211> LENGTH: 21
<212> TYPE: DNA
<213> ORGANISM: Artificial
<220> FEATURE:
<223> OTHER INFORMATION: CXCL11 fwd primer

<400> SEQUENCE: 23
cagaattcca ctgcccaaag g                                      21

<210> SEQ ID NO 24
<211> LENGTH: 23
<212> TYPE: DNA
<213> ORGANISM: Artificial
<220> FEATURE:
<223> OTHER INFORMATION: CXCL11 rev primer

<400> SEQUENCE: 24
gtaaactccg atggtaacca gcc                                    23

<210> SEQ ID NO 25
<211> LENGTH: 19
<212> TYPE: DNA
<213> ORGANISM: Artificial
<220> FEATURE:
<223> OTHER INFORMATION: CD80 fwd primer

<400> SEQUENCE: 25
ctgctttgcc ccaagatgc                                         19

<210> SEQ ID NO 26
<211> LENGTH: 21
<212> TYPE: DNA
<213> ORGANISM: Artificial
<220> FEATURE:
<223> OTHER INFORMATION: CD80 rev primer

<400> SEQUENCE: 26
cagatctttt cagccccttg c                                      21

<210> SEQ ID NO 27
<211> LENGTH: 20
<212> TYPE: DNA
<213> ORGANISM: Artificial
<220> FEATURE:
<223> OTHER INFORMATION: IL6 fwd primer

<400> SEQUENCE: 27 cccectagtt gtgtcttgcc                                        20

<210> SEQ ID NO 28
<211> LENGTH: 20
<212> TYPE: DNA
<213> ORGANISM: Artificial
<220> FEATURE:
<223> OTHER INFORMATION: IL6 rev primer

<400> SEQUENCE: 28
ctttgttgga gggtgagggt                                        20

<210> SEQ ID NO 29
```

```
<211> LENGTH: 21
<212> TYPE: DNA
<213> ORGANISM: Artificial
<220> FEATURE:
<223> OTHER INFORMATION: IL-1beta fwd primer

<400> SEQUENCE: 29
ggcattgatc tggttcatcc a                                          21

<210> SEQ ID NO 30
<211> LENGTH: 22
<212> TYPE: DNA
<213> ORGANISM: Artificial
<220> FEATURE:
<223> OTHER INFORMATION: IL-1beta rev primer

<400> SEQUENCE: 30
ggcagagaac atacggtatg ca                                         22

<210> SEQ ID NO 31
<211> LENGTH: 20
<212> TYPE: DNA
<213> ORGANISM: Artificial
<220> FEATURE:
<223> OTHER INFORMATION: CCL20 fwd primer

<400> SEQUENCE: 31
agcaggaagt tttccttgcg                                            20

<210> SEQ ID NO 32
<211> LENGTH: 19
<212> TYPE: DNA
<213> ORGANISM: Artificial
<220> FEATURE:
<223> OTHER INFORMATION: CCL20 rev primer

<400> SEQUENCE: 32
agaaggcgtg ttgccacat                                             19

<210> SEQ ID NO 33
<211> LENGTH: 20
<212> TYPE: DNA
<213> ORGANISM: Artificial
<220> FEATURE:
<223> OTHER INFORMATION: TNFalpha fwd primer

<400> SEQUENCE: 33
cctccagggt cctacacaca                                            20

<210> SEQ ID NO 34
<211> LENGTH: 20
<212> TYPE: DNA
<213> ORGANISM: Artificial
<220> FEATURE:
<223> OTHER INFORMATION: TNFalpha rev primer

<400> SEQUENCE: 34
ttggggacac acaagcatca                                            20

<210> SEQ ID NO 35
<211> LENGTH: 24
<212> TYPE: DNA
<213> ORGANISM: Artificial
<220> FEATURE:
<223> OTHER INFORMATION: IDO1 fwd primer

<400> SEQUENCE: 35
```
agcgcgagag ctattctaga ctgt                                          24

<210> SEQ ID NO 36
<211> LENGTH: 24
<212> TYPE: DNA
<213> ORGANISM: Artificial
<220> FEATURE:
<223> OTHER INFORMATION: IDO1 rev primer

<400> SEQUENCE: 36
agaaaccaag ttgcccgttc ctct                                          24

<210> SEQ ID NO 37
<211> LENGTH: 23
<212> TYPE: DNA
<213> ORGANISM: Artificial
<220> FEATURE:
<223> OTHER INFORMATION: CCL5 fwd primer

<400> SEQUENCE: 37
tgggagagac cctatgacca gga                                           23

<210> SEQ ID NO 38
<211> LENGTH: 22
<212> TYPE: DNA
<213> ORGANISM: Artificial
<220> FEATURE:
<223> OTHER INFORMATION: CCL5 rev primer

<400> SEQUENCE: 38
ggcagttgat ctgagctggg ca                                            22

<210> SEQ ID NO 39
<211> LENGTH: 22
<212> TYPE: DNA
<213> ORGANISM: Artificial
<220> FEATURE:
<223> OTHER INFORMATION: CXCL10 fwd primer

<400> SEQUENCE: 39
accactctct ctccttccaa ct                                            22

<210> SEQ ID NO 40
<211> LENGTH: 23
<212> TYPE: DNA
<213> ORGANISM: Artificial
<220> FEATURE:
<223> OTHER INFORMATION: CXCL10 rev primer

<400> SEQUENCE: 40
taggccaagc tctgttatgc tac                                           23

<210> SEQ ID NO 41
<211> LENGTH: 22
<212> TYPE: DNA
<213> ORGANISM: Artificial
<220> FEATURE:
<223> OTHER INFORMATION: CXCL11 fwd primer

<400> SEQUENCE: 41
tcccaccaac actcacataa gg                                            22

<210> SEQ ID NO 42
<211> LENGTH: 24
<212> TYPE: DNA

```
<213> ORGANISM: Artificial
<220> FEATURE:
<223> OTHER INFORMATION: CXCL11 rev primer

<400> SEQUENCE: 42
ttaatgggta ggtgggaaag acag                                    24

<210> SEQ ID NO 43
<211> LENGTH: 20
<212> TYPE: DNA
<213> ORGANISM: Artificial
<220> FEATURE:
<223> OTHER INFORMATION: CD80 fwd primer

<400> SEQUENCE: 43
aggccccttc tgccaataca                                         20

<210> SEQ ID NO 44
<211> LENGTH: 22
<212> TYPE: DNA
<213> ORGANISM: Artificial
<220> FEATURE:
<223> OTHER INFORMATION: CD80 rev primer

<400> SEQUENCE: 44
agtttgtggc agagcttagt gg                                      22
```